(12) United States Patent
Dusch

(10) Patent No.: US 8,883,458 B2
(45) Date of Patent: *Nov. 11, 2014

(54) PROCESS FOR PREPARING L-AMINO ACIDS USING IMPROVED STRAINS OF THE ENTEROBACTERIACEAE FAMILY

(75) Inventor: Nicole Dusch, Werther (DE)

(73) Assignee: Evonik Degussa GmbH, Essen (DE)

( * ) Notice: Subject to any disclaimer, the term of this patent is extended or adjusted under 35 U.S.C. 154(b) by 969 days.

This patent is subject to a terminal disclaimer.

(21) Appl. No.: 12/692,131

(22) Filed: Jan. 22, 2010

(65) Prior Publication Data

US 2011/0053227 A1      Mar. 3, 2011

Related U.S. Application Data

(62) Division of application No. 11/413,056, filed on Apr. 28, 2006, now abandoned.

(30) Foreign Application Priority Data

May 3, 2005 (DE) .......................... 10 2005 020 538

(51) Int. Cl.
- C12P 13/04 (2006.01)
- C12P 13/08 (2006.01)
- C07K 14/245 (2006.01)
- C07H 21/00 (2006.01)
- C12N 1/21 (2006.01)
- C12N 9/00 (2006.01)
- C12N 15/00 (2006.01)
- C12P 21/00 (2006.01)

(52) U.S. Cl.
CPC ............... *C12P 13/04* (2013.01); *C07K 14/245* (2013.01); *C12P 13/08* (2013.01)
USPC ..... 435/106; 435/115; 435/252.3; 435/320.1; 435/69.1; 435/183; 536/23.2

(58) Field of Classification Search
USPC .......... 435/106, 115, 252.3, 69.1, 183, 320.1; 530/350; 536/23.2
See application file for complete search history.

(56) References Cited

U.S. PATENT DOCUMENTS

| | | | |
|---|---|---|---|
| 5,175,107 A | 12/1992 | Debabov et al. | 435/252.33 |
| 6,667,166 B2 | 12/2003 | Thierbach et al. | 435/106 |
| 7,470,524 B2 | 12/2008 | Rybak et al. | 435/106 |

FOREIGN PATENT DOCUMENTS

| | | |
|---|---|---|
| WO | WO 03/008607 A | 1/2003 |
| WO | WO 2004/087937 A | 10/2004 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Sousa et al., Microbiology 148(Pt5):1291-1303, 2002.*
Zhou et al., Cell Mol Life Sci 63(19-20):2260-2290, 2006.*
Kozak, M., Gene 234:187-208, 1999.*
Gimenez, Rosa et al., "The gene yjcG, cotranscribed with the gene acs, encodes an acetate permease in *Escherichia coli*," *Journal of Bacteriology*, vol. 185, No. 21, Nov. 2003, pp. 6448-6455, ISSN: 0021-9193.
Jin, Q. et al., "Cation/acetate symporter actP (Acetate transporter actP) (Acetate permease)," Database UniProt, May 1, 2005, Database accessioin No. Q83P94, *the complete document.
McClelland, M. et al., "Cation/acetate symporter actP (Acetate transporter actP) (Acetate permease)," Database UniProt., May 1, 2005, Database accession No. Q8ZKF8, *the complete document.
Blattner et al., UniProt accession No. P32705, 1993.
Blattner et al., GenBank accession No. U00096, 1993.

* cited by examiner

*Primary Examiner* — Delia Ramirez
(74) *Attorney, Agent, or Firm* — Smith, Gambrell & Russell, LLP

(57) ABSTRACT

The invention relates to a process for preparing L-amino acids by fermenting recombinant microorganisms of the Enterobacteriaceae family, characterized in that
a) the desired L-amino acid-producing microorganisms, in which the yjcG-ORF, or nucleotide sequences or alleles encoding the gene product, is/are enhanced, in particular overexpressed, is cultured in a medium under conditions under which the desired L-amino acid is accumulated in the medium or in the cells, and
b) the desired L-amino acid is isolated, with, where appropriate, constituents of the fermentation broth, and/or the biomass remaining in its/their entirety or in portions (from ≥0 to 100%) in the isolated product or being removed completely.

16 Claims, 1 Drawing Sheet

Map of the plasmid pMW218yjcG
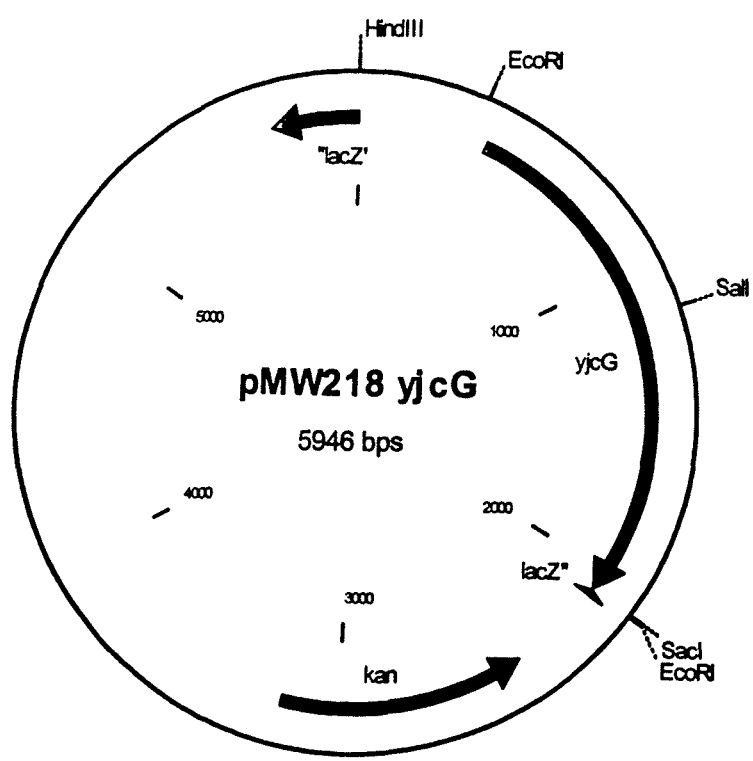

PROCESS FOR PREPARING L-AMINO ACIDS USING IMPROVED STRAINS OF THE ENTEROBACTERIACEAE FAMILY

CROSS REFERENCE TO RELATED APPLICATIONS

This application is a division of U.S. patent application Ser. No. 11/413,056, filed 28 Apr. 2006, now abandoned, and claims the benefit of DE 102005020538.0, filed 3 May 2005, both of which are herein incorporated by reference in their entirety.

This invention relates to a process for preparing L-amino acids, in particular L-threonine, using recombinant microorganisms strains of the Enterobacteriaceae family in which the open reading frame (ORF) designated yjcG is enhanced, in particular overexpressed, and to said microorganisms.

PRIOR ART

L-Amino acids, in particular L-threonine, are used in human medicine and in the pharmaceutical industry, in the foodstuff industry and, very particularly, in animal nutrition.

It is known that L-amino acids can be prepared by fermenting Enterobacteriaceae strains, in particular *Escherichia coli* (*E. coli*) and *Serratia marcescens*. Because of the great importance, efforts are continually being made to improve the preparation methods. Methodological improvements can concern measures relating to fermentation technology, such as stirring or supplying with oxygen, or the composition of the nutrient media, such as the sugar concentration during the fermentation, or the working-up to the product form, for example by means of ion exchange chromatography, or the intrinsic performance properties of the microorganism itself.

Methods of mutagenesis, selection and mutant choice are used for improving the performance properties of these microorganisms. This thereby results in strains which are resistant to antimetabolites, such as the threonine analog α-amino-β-hydroxyvaleric acid (AHV), or auxotrophic for metabolites of regulatory importance and produce L-amino acids such as L-threonine.

For a number of years now, recombinant DNA methods have also been used for improving L-amino acid-producing strains of the Enterobacteriaceae family by amplifying individual amino acid biosynthesis genes and investigating the effect on production. Compiled information on the cell biology and molecular biology of *Escherichia coli* and *Salmonella* can be found in Neidhardt (ed): *Escherichia coli* and *Salmonella*, Cellular and Molecular Biology, $2^{nd}$ edition, ASM Press, Washington, D.C., USA, (1996).

OBJECT OF THE INVENTION

The inventors have set the object of providing novel measures for improving the fermentative preparation of L-amino acids, in particular L-threonine.

DESCRIPTION OF THE INVENTION

The invention relates to recombinant microorganisms of the Enterobacteriaceae family which contain an enhanced or overexpressed open reading frame yjcG, which encodes a polypeptide which is annotated as being acetate permease, or nucleotide sequences encoding its gene product and which display an improved ability to form and accumulate L-amino acids, in particular L-threonine.

In each case, the microorganisms which are not recombinant for the yjcG-ORF, which do not contain any enhanced yjcG-ORF, and on which the measures of the invention are performed are used as the starting point for the comparison.

These recombinant microorganisms include, in particular, microorganisms of the Enterobacteriaceae family in which a polynucleotide which encodes a polypeptide whose amino acid sequence is at least 90%, in particular at least 95%, preferably at least 98%, are at least 99%, particularly preferably 99.8% and very particularly preferably 100%, identical to an amino acid sequence selected from the group SEQ ID No. 2, SEQ ID No. 4 and SEQ ID No. 6 is enhanced.

Said microorganisms contain enhanced or overexpressed polynucleotides selected from the group:
a) polynucleotide having a nucleotide sequence, selected from SEQ ID No. 1, SEQ ID No. 3 and SEQ ID No. 5 and the nucleotide sequences complementary thereto;
b) polynucleotide having a nucleotide sequence which corresponds to SEQ ID No. 1, SEQ ID No. 3 or SEQ ID No. 5 within the limits of the degeneracy of the genetic code;
c) polynucleotide sequence having a sequence which hybridizes, under stringent conditions, with the sequence which is complementary to the sequence SEQ ID No. 1, SEQ ID No. 3 or SEQ ID No. 5, with the stringent conditions preferably being achieved by means of a washing step in which the temperature extends over a range of from 64° C. to 68° C. and the salt concentration of the buffer extends over a range of from 2×SSC to 0.1×SSC;
d) polynucleotide having a sequence SEQ ID No. 1, SEQ ID No. 3 or SEQ ID No. 5 which contains functionally neutral sense mutants,
with the polynucleotides preferably encoding an acetate permease.

The invention also relates to a process for fermentatively preparing L-amino acids, in particular L-threonine, using recombinant microorganisms of the Enterobacteriaceae family which, in particular, already produce L-amino acids and in which at least the open reading frame (ORF) having the designation yjcG, or nucleotide sequences encoding its gene product, is or are enhanced.

Preference is given to using the microorganisms which are described.

When L-amino acids or amino acids are mentioned in that which follows, this thereby means one or more amino acids, including their salts, selected from the group L-asparagine, L-threonine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine and L-homoserine. L-threonine is particularly preferred.

In this connection, the term "enhancement" describes the increase, in a microorganism, of the intracellular activity or concentration of one or more enzymes or proteins which are encoded by the corresponding DNA, with, for example, the copy number of the gene or genes, or of the ORF or ORFs, being increased by at least one (1) copy, use being made of a strong promoter operatively linked to the gene or of a gene or allele or ORF which encodes a corresponding enzyme or protein having a high activity, and, where appropriate, these measures being combined.

A segment of a nucleotide sequence which encodes, or can encode, a protein and/or a polypeptide or ribonucleic acid to which the prior art is unable to assign any function is designated an open reading frame (ORF). After a function has been assigned to the nucleotide sequence segment in question, this segment is generally referred to as being a gene. Alleles are generally understood as being alternative forms of a given gene. The forms are distinguished by differences in the nucleotide sequence.

In general, the protein, or the ribonucleic acid, encoded by a nucleotide sequence, i.e. an ORF, a gene or an allele, is designated a gene product.

The enhancement measures, in particular overexpression, generally increase the activity or concentration of the corresponding protein by at least 10%, 25%, 50%, 75%, 100%, 150%, 200%, 300%, 400% or 500%, maximally up to 1000% or 2000%, based on that of the wild-type protein or on the activity or concentration of the protein in the parent strain or microorganism which is not recombinant for the corresponding enzyme or protein. The non-recombinant microorganism or parent strain is understood as being the microorganism on which the measures according to the invention are performed.

The invention relates to a process for preparing L-amino acids by fermenting recombinant microorganisms of the Enterobacteriaceae family, characterized in that
a) the desired L-amino acid-producing microorganisms, in which the open reading frame yjcG, or nucleotide sequences or alleles encoding the gene product, is/are enhanced, in particular overexpressed, are cultured in a medium under conditions under which the desired L-amino acid is accumulated in the medium or in the cells, and
b) the desired L-amino acid is isolated, with, where appropriate, the fermentation broth constituents and/or the biomass remaining in its/their entirety or in portions (from ≥0 to 100%) in the isolated product or being removed completely.

The microorganisms which have an enhanced or overexpressed open reading frame (ORF) designated yjcG, and which are in particular recombinant, are likewise part of the subject matter of the present invention, can produce L-amino acids from glucose, sucrose, lactose, fructose, maltose, molasses, where appropriate starch and where appropriate cellulose or from glycerol and ethanol. The microorganisms are representatives of the Enterobacteriaceae family and are selected from the genera *Escherichia*, *Erwinia*, *Providencia* and *Serratia*. The genera *Escherichia* and *Serratia* are preferred. The species *Escherichia coli* may be mentioned, in particular, in the case of the genus *Escherichia* while the species *Serratia marcescens* may be mentioned, in particular, in connection with the genus *Serratia*.

In general, recombinant microorganisms are generated by means of transformation, transduction or conjugation, or a combination of these methods, with a vector which contains the desired ORF, the desired gene, an allele of this ORF or gene, or parts thereof, and/or a promoter which potentiates the expression of the ORF or gene. This promoter can be the promoter which has been produced by enhancing mutation from the endogenous regulatory sequence located upstream of the gene or ORF; alternatively, an efficient promotor has been fused to the gene or ORF.

Examples of strains of the genus *Escherichia*, in particular of the species *Escherichia coli*, which are suitable as parent strain, which produce L-threonine, in particular, and which are to be mentioned are:

| | |
|---|---|
| *Escherichia coli* H4581 | (EP 0 301 572) |
| *Escherichia coli* KY10935 | (Bioscience Biotechnology and Biochemistry 61(11): 1877-1882 (1997) |
| *Escherichia coli* VNIIgenetica MG442 | (U.S. Pat. No. 4,278,765) |
| *Escherichia coli* VNIIgenetica M1 | (U.S. Pat. No. 4,321,325) |
| *Escherichia coli* VNIIgenetica 472T23 | (U.S. Pat. No. 5,631,157) |
| *Escherichia coli* BKIIM B-3996 | (U.S. Pat. No. 5,175,107) |
| *Escherichia coli* cat 13 | (WO 98/04715) |
| *Escherichia coli* KCCM-10132 | (WO 00/09660) |

Examples of L-threonine-producing strains of the genus *Serratia*, in particular of the species *Serratia marcescens*, which are suitable as parent strain and which are to be mentioned are:

*Serratia marcescens* HNr21 (Applied and Environmental Microbiology 38(6): 1045-1051 (1979))

*Serratia marcescens* TLr156 (Gene 57(2-3): 151-158 (1987))

*Serratia marcescens* T-2000 (Applied Biochemistry and Biotechnology 37(3): 255-265 (1992))

L-Threonine-producing strains of the Enterobacteriaceae family preferably possess, inter alia, one or more of the genetic or phenotypic features selected from the group: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to cyclopentanecarboxylic acid, resistance to rifampicin, resistance to valine analogs such as valine hydroxamate, resistance to purine analogs, such as 6-dimethylaminopurine, requirement for L-methionine, possible partial and compensatable requirement for L-isoleucine, requirement for mesodiaminopimelic acid, auxotrophy in regard to threonine-containing dipeptides, resistance to L-threonine, resistance to threonine raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, possible ability to utilize sucrose, enhancement of the threonine operon, enhancement of homoserine dehydrogenase I-aspartate kinase I, preferably of the feedback-resistant form, enhancement of homoserine kinase, enhancement of threonine synthase, enhancement of aspartate kinase, possibly of the feedback-resistant form, enhancement of aspartate semialdehyde dehydrogenase, enhancement of phosphoenolpyruvate carboxylase, possibly of the feedback-resistant form, enhancement of phosphoenolpyruvate synthase, enhancement of transhydrogenase, enhancement of the RhtB gene product, enhancement of the RhtC gene product, enhancement of the YfiK gene product, enhancement of a pyruvate carboxylase and attenuation of acetic acid formation.

It has been found that, following overexpression of the gene or the open reading frame (ORF) yjcG, or its alleles, microorganisms of the Enterobacteriaceae family display an improved ability to form and accumulate L-amino acids, in particular L-threonine.

The nucleotide sequences of the *Escherichia coli* genes or open reading frames (ORFs) belong to the prior art and can be obtained from the *Escherichia coli* genome sequence published by Blattner et al. (Science 277: 1453-1462 (1997)). It is known that endogenous enzymes (methionine aminipeptidase) are able to cleave off the N-terminal amino acid methionine.

The nucleotide sequences for the yjcG-ORF from *Salmonella typhimirium* (Accession No.: NC_003197 (Region 4511508-4513157)) and *Shigella flexneri* (Accession No.:

NC_004337 (Region 4293843-4295492)), which likewise belong to the Enterobacteriaceae family, have also been disclosed.

The yjcG-ORF of *Escherichia coli* K12 is described, inter alia, by the following data:

Gimenez et al. (Journal of Microbiology 185(21): 6448-55 (2003)) describe the *Escherichia coli* open reading frame yjcG, which encodes a protein having the function of an acetate permease from the solute: sodium symporter (SSS) family, and propose the gene name actP; the gene is cotranscribed with acs, which encodes an acetyl coenzyme A synthetase; the permease is highly specific for short-chain aliphatic monocarboxylates and, in addition to acetate, also transports glycolate in a quantity sufficient for growth, as well as small carboxylates such as propionate.

| Accession No.: | NC000913 (Region 4281276-4282925) |
|---|---|
| Alternative gene name: | b4067, actP |

The nucleic acid sequences can be obtained from the databases belonging to the National Center for Biotechnology Information (NCBI) of the National Library of Medicine (Bethesda, Md., USA), the nucleic acid sequence database of the European Molecular Biology Laboratories (EMBL, Heidelberg, Germany or Cambridge, UK) or the Japanese DNA database (DDBJ, Mishima, Japan).

For the sake of greater clarity, the known nucleotide sequence for the yjcG-ORF of *Escherichia coli* is depicted under SEQ ID No. 1 and the known sequences for the yjcG-ORF of *Salmonella typhimurium* or *Shigella flexneri* under SEQ ID No. 3 and, respectively, SEQ ID No. 5. The proteins encoded by these reading frames are depicted as SEQ ID No. 2, SEQ ID No. 4 and SEQ ID No. 6.

The open reading frames described in the passages indicated can be used in accordance with the invention. In addition, it is possible to use alleles of the genes or open reading frames, which result from the degeneracy of the genetic code or as a consequence of functionally neutral sense mutations. Preference is given to using endogenous genes or endogenous open reading frames.

"Endogenous genes" or "endogenous nucleotide sequences" are understood as being the genes or open reading frames or alleles or nucleotide sequences which are present in a species population.

The alleles of the yjcG-ORF, which contain functionally neutral sense mutations, include, inter alia, those which lead to at most 60 or to at most 50 or to at most 40 or to at most 30 or to at most 20, preferably to at most 10 or to at most 5, very particularly preferably to at most 3 or to at most 2, or to at least one, conservative amino acid substitution in the protein which they encode.

In the case of the aromatic amino acids, the substitutions are said to be conservative when phenylalanine, tryptophan and tyrosine are substituted for each other. In the case of the hydrophobic amino acids, the substitutions are said to be conservative when leucine, isoleucine and valine are substituted for each other. In the case of the polar amino acids, the substitutions are said to be conservative when glutamine and asparagine are substituted for each other. In the case of the basic amino acids, the substitutions are said to be conservative when arginine, lysine and histidine are substituted for each other. In the case of the acid amino acids, the substitutions are said to be conservative when aspartic acid and glutamic acid are substituted for each other. In the case of the hydroxyl group-containing amino acids, the substitutions are said to be conservative when serine and threonine are substituted for each other.

In the same way, it is also possible to use nucleotide sequences which encode variants of said proteins, which variants additionally contain an extension or truncation by at least one (1) amino acid at the N terminus or C terminus. This extension or truncation amounts to not more than 60, 50, 40, 30, 20, 10, 5, 3 or 2 amino acids or amino acid residues.

The suitable alleles also include those which encode proteins in which at least one (1) amino acid has been inserted or deleted. The maximum number of such changes, termed indels, can affect 2, 3, 5, 10, 20, but in no case more than 30, amino acids.

The suitable alleles furthermore include those which can be obtained by means of hybridization, in particular under stringent conditions, using SEQ ID No. 1, SEQ ID No. 3 or SEQ ID No. 5 or parts thereof, in particular the coding regions or the sequences which are complementary thereto.

The skilled person finds instructions for identifying DNA sequences by means of hybridization in, inter alia, the manual "The DIG System Users Guide for Filter Hybridization" supplied by Boehringer Mannheim GmbH (Mannheim, Germany, 1993) and Liebl et al. (International Journal of Systematic Bacteriology 41: 255-260 (1991)). The hybridization takes place under stringent conditions, that is the only hybrids formed are those in which the probe and target sequence, i.e. the polynucleotides treated with the probe, are at least 80% identical. It is known that the stringency of the hybridization, including the washing steps, is influenced and/or determined by varying the buffer composition, the temperature and the salt concentration. In general, the hybridization reaction is carried out at a stringency which is relatively low as compared with that of the washing steps (Hybaid Hybridization Guide, Hybaid Limited, Teddington, UK, 1996).

For example, a buffer corresponding to 5×SSC buffer can be used for the hybridization reaction at a temperature of approx. 50° C.-68° C. Under these conditions, probes can also hybridize with polynucleotides which possess less than 70% identity with the sequence of the probe. These hybrids are less stable and are removed by washing under stringent conditions. This can be achieved, for example, by lowering the salt concentration down to 2×SSC and, where appropriate, subsequently to 0.5×SSC (The DIG System User's Guide for Filter Hybridization, Boehringer Mannheim, Mannheim, Germany, 1995) with the temperature being adjusted to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. By means of increasing the hybridization temperature stepwise, in steps of approx. 1-2° C., from 50° C. to 68° C., it is possible to isolate polynucleotide fragments which, for example, possess at least 80%, or at least 90%, at least 91%, at least 92%, at least 93%, at least 94%, at least 95%, at least 96%, at least 97%, at least 98%, or at least 99%, identity with the sequence of the probe employed or with the nucleotide sequences shown in SEQ ID No. 1, SEQ ID No. 3 or SEQ ID No. 5. Additional instructions for the hybridization can be obtained commercially in the form of what are termed kits (e.g. DIG Easy Hyb from Roche Diagnostics GmbH, Mannheim, Germany, Catalog No. 1603558).

In order to achieve enhancement, it is possible, for example, to increase the expression of the genes or open reading frames or alleles or to increase the catalytic properties of the protein. Both measures can be combined, where appropriate.

In order to achieve overexpression, the copy number of the corresponding genes or open reading frames can be increased, for example, or the promoter region and regulatory region or the ribosome binding site which is located upstream of the structural gene can be mutated. Expression cassettes which are incorporated upstream of the structural gene act in the same manner. It is also possible to increase expression during the course of the fermentative L-threonine production through inducible promoters; in addition, using promoters for gene expression which permits a different chronological gene expression can also be advantageous. At the level of the translational regulation of gene expression, it is possible to increase the frequency of initiation (binding of the ribosome to the mRNA) or the rate of elongation (elongation phase). Expression is likewise improved by means of measures for extending the lifespan of the mRNA. Furthermore, the enzyme activity is also enhanced by preventing the enzyme protein from being broken down. The ORFs, genes or gene constructs can either be present in plasmids having different copy numbers or be integrated, and amplified, in the chromosome. Alternatively, overexpression of the genes concerned can also be achieved by altering the composition of the media and the conduct of the culture.

Methods for overexpression are adequately described in the prior art, for example in Makrides et al. (Microbiological Reviews 60 (3), 512-538 (1996)). Using vectors increases the copy number by at least one (1) copy. The vectors used can be plasmids as described, for example, in U.S. Pat. No. 5,538,873. The vectors used can also be phages, for example phage Mu, as described in EP 0332448, or phage lambda (λ). The copy number can also be increased by incorporating an additional copy into another site in the chromosome, for example in to the att site of phage λ (Yu and Court, Gene 223, 77-81 (1998)). U.S. Pat. No. 5,939,307 reports that it was possible to increase the expression by incorporating expression cassettes or promoters, such as the tac promoter, the trp promoter, the l pp promoter, or the $P_L$ promoter or $P_R$ promoter of phage λ, upstream, for example, of the chromosomal threonine operon. In the same way, it is possible to use the phage T7 promoters, the gearbox promoters or the nar promoter. Such expression cassettes or promoters can also be used, as described in EP 0 593 792, to overexpress plasmid-bound genes. Using the $lacI^Q$ allele in turn makes it possible to control the expression of plasmid-bound genes (Glascock and Weickert, Gene 223, 221-231 (1998)). It is furthermore possible for the activity of the promoters to be increased by modifying their sequence by means of one or more nucleotide substitutions, by means of (an) insertion(s) and/or by means of (a) deletion(s). A different chronological gene expression can be achieved, for example, as described in Walker et al. (Journal of Bacteriology 181: 1269-80 (1999)), by using the growth phase-dependent fis promoter. The rate of elongation is influenced by the codon usage; gene expression can be enhanced by using codons for tRNAs which occur frequently in the parent strain.

The skilled person can find general instructions in this regard in, inter alia, Chang and Cohen (Journal of Bacteriology 134: 1141-1156 (1978)), Hartley and Gregori (Gene 13: 347-353 (1981)), Amann and Brosius (Gene 40: 183-190 (1985)), de Broer et al. (Proceedings of the National Academy of Sciences of the United States of America 80: 21-25 (1983)), LaVallie et al. (BIO/TECHNOLOGY 11: 187-193 (1993)), in PCT/US97/13359, Llosa et al. (Plasmid 26: 222-224 (1991)), Quandt and Klipp (Gene 80: 161-169 (1989)), Hamilton et al. (Journal of Bacteriology 171: 4617-4622 (1989)), Jensen and Hammer (Biotechnology and Bioengineering 58: 191-195 (1998)) and known textbooks of genetics and molecular biology.

Plasmid vectors which can be replicated in Enterobacteriaceae, such as pACYC184-derived cloning vectors (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences USA 80(21): 6557-6561 (1983)) can be used. In a process according to the invention, it is possible to use a strain which is transformed with a plasmid vector which carries at least the yjcG-ORF, or nucleotide sequences, or alleles, which encode its gene product.

The term "transformation" is understood as meaning the uptake of an isolated nucleic acid by a host (microorganism).

It is also possible to use sequence exchange (Hamilton et al.; Journal of Bacteriology 171: 4617-4622 (1989)), conjugation or transduction to transfer mutations, which affect the expression of the given genes or open reading frames, into different strains.

More detailed explanations of the concepts of genetics and molecular biology can be found in known textbooks of genetics and molecular biology such as the textbook by Birge (Bacterial and Bacteriophage Genetics, $4^{th}$ ed., Springer Verlag, New York (USA), 2000) or the textbook by Berg, Tymoczko and Stryer (Biochemistry, $5^{th}$ ed., Freeman and Company, New York (USA), 2002) or the manual by Sambrook et al. (Molecular Cloning, A Laboratory Manual, (3-Volume Set), Cold Spring Harbor Laboratory Press, Cold Spring Harbor (USA), 2001).

Furthermore, when using strains of the Enterobacteriaceae family to produce L-amino acids, in particular L-threonine, it can be advantageous, in addition to potentiating the open reading frame yjcG, to enhance one or more enzymes of the known threonine biosynthesis pathway or enzymes of anaplerotic metabolism or enzymes for producing reduced nicotinamide adenine dinucleotide phosphate or enzymes of glycolysis or PTS enzymes or enzymes of sulfur metabolism. Using endogenous genes is generally preferred.

Thus, it is possible, for example, to simultaneously enhance, in particular overexpress, one or more of the genes selected from the group at least one gene of the thrABC operon encoding aspartate kinase, homoserine dehydrogenase, homoserine kinase and threonine synthase (U.S. Pat. No. 4,278,765), the pyruvate carboxylase-encoding *Corynebacterium glutamicum* pyc gene (WO 99/18228), the phosphoenolpyruvate synthase-encoding pps gene (Molecular and General Genetics 231(2): 332-336 (1992); WO 97/08333), the phosphoenolpyruvate carboxylase-encoding ppc gene (WO 02/064808), the pntA and pntB genes encoding the subunits of transhydrogenase (European Journal of Biochemistry 158: 647-653 (1986); WO 95/11985), the rhtC gene encoding the threonine resistance-mediating protein (EP-A-1 013 765), the threonine export carrier protein-encoding *Corynebacterium glutamicum* thrE gene (WO 01/92545), the glutamate dehydrogenase-encoding gdhA gene (Nucleic Acids Research 11: 5257-5266 (1983); Gene 23: 199-209 (1983); DE19907347), the ptsHIcrr operon ptsH gene encoding the phosphohistidine protein hexose phosphotransferase of the PTS phosphotransferase system (WO 03/004674), the ptsHIcrr operon ptsI gene encoding enzyme I of the PTS phosphotransferase system (WO 03/004674), the ptsHIcrr operon crr gene encoding the glucose-specific IIA component of the PTS phosphotransferase system (WO 03/004674), the ptsG gene encoding the glucose-specific IIBC component (WO 03/004670), the cysteine synthase A-encoding cysK gene (WO 03/006666), the cysB gene encoding the regulator of the cys regulon (WO 03/006666), the cysJIH operon cysJ gene encoding the NADPH sulfite reductase flavoprotein (WO 03/006666), the cysJIH operon cysI gene encoding the NADPH sulfite reductase hemoprotein (WO 03/006666), the adenylyl sulfate reductase-encoding cysJIH operon cysH gene (WO 03/006666), the sucABCD operon sucA gene encoding the decarboxylase subunit of 2-ketoglutarate dehydrogenase (WO 03/008614), the sucABCD operon sucB gene encoding the dihydrolipoyl-transsuccinase E2 subunit of 2-ketoglutarate dehydrogenase (WO 03/008614), the sucABCD operon sucC gene encoding the β-subunit of succinyl-CoA synthetase (WO 03/008615), the sucABCD operon sucD gene encoding the α-subunit of succinyl-CoA synthetase (WO 03/008615), the gene product of the *Escherichia coli* yibD open reading frame (ORF) (Accession Number AE000439 of the National Center for Biotechnology Information (NCBI, Bethesda, Md., USA, DE102004005836.9)), and the gene acs encoding the acetyl coenzyme A synthetase (Journal of Bacteriology 177(10): 2878-86 (1995)).

Furthermore, for the purpose of producing L-amino acids, in particular L-threonine, it can be advantageous, in addition to enhancing the open reading frame yjcG, to attenuate, in particular eliminate or reduce the expression of one or more of the genes selected from the group the threonine dehydrogenase-encoding tdh gene (Journal of Bacteriology 169: 4716-4721 (1987)), the malate dehydrogenase (E.C. 1.1.1.37)-encoding mdh gene (Archives in Microbiology 149: 36-42 (1987)), the gene product of the *Escherichia coli* yjfA open reading frame (ORF) (Accession Number AAC77180 of the National Center for Biotechnology Information (NCBI, Bethesda, Md., USA), (WO 02/29080), the gene product of the *Escherichia coli* ytfP open reading frame (ORF) (Accession Number AAC77179 of the National Center for Biotechnology Information (NCBI, Bethesda, Md., USA), WO 02/29080)), the pckA gene encoding the enzyme phosphoenolpyruvate carboxykinase (WO 02/29080), the pyruvate oxidase-encoding poxB gene (WO 02/36797), the dgsA gene (WO 02/081721), which is also known under the name mlc gene, encoding the DgsA regulator of the phosphotransferase system, the fruR gene (WO 02/081698), which is also known under the name cra gene, encoding the fructose repressor, the rpoS gene (WO 01/05939), which is also known under the name katF gene, encoding the sigma$^{38}$ factor, and the aspartate ammonium lyase-encoding aspA gene (WO 03/008603).

In this context, the term "attenuation" describes the reduction or abolition, in a microorganism, of the intra-cellular activity or concentration of one or more enzymes or proteins which are encoded by the corresponding DNA, by, for example, using a weaker promoter than in the parent strain or microorganism not recombinant for the corresponding enzyme or protein, or a gene or allele which encodes a corresponding enzyme or protein having a lower activity, or inactivating the corresponding enzyme or protein, or the open reading frame or gene, and, where appropriate, combining these measures.

In general, the attenuation measures lower the activity or concentration of the corresponding protein down to from 0 to 75%, from 0 to 50%, from 0 to 25%, from 0 to 10% or from 0 to 5% of the activity or concentration of the wild-type protein or of the activity or concentration of the protein for the parent strain or microorganism which is not recombinant for the corresponding enzyme or protein. The parent strain or microorganism which is not recombinant is understood as being the microorganism on which the measures according to the invention are performed.

In order to achieve an attenuation, for example the expression of the genes or open reading frames, or the catalytic properties of the enzyme proteins, can be reduced or abolished. Where appropriate, both measures can be combined.

The gene expression can be reduced by carrying out the culture in a suitable manner, by genetically altering (mutating) the signal structures for the gene expression or by means of the antisense RNA technique. Signal structures for the gene expression are, for example, repressor genes, activator genes, operators, promoters, attenuators, ribosome binding sites, the start codon and terminators. The skilled person can find information in this regard in, inter alia and for example, Jensen and Hammer (Biotechnology and Bioengineering 58: 191-195 (1998)), in Carrier and Keasling (Biotechnology Progress 15: 58-64 (1999)), in Franch and Gerdes (Current Opinion in Microbiology 3: 159-164 (2000)) and in well known textbooks of genetics and molecular biology such as the textbook by Knippers ("Molekulare Genetik [Molecular Genetics]", 6th edition, Georg Thieme Verlag, Stuttgart, Germany, 1995) or that by Winnacker ("Gene and Klone [Genes and Clones]", VCH Verlagsgesellschaft, Weinheim, Germany, 1990).

Mutations which lead to a change or reduction in the catalytic properties of enzyme proteins are known from the prior art. Examples which may be mentioned are the articles by Qiu and Goodman (Journal of Biological Chemistry 272: 8611-8617 (1997)), Yano et al. (Proceedings of the National Academy of Sciences of the United States of America 95: 5511-5515 (1998)) and Wente and Schachmann (Journal of Biological Chemistry 266: 20833-20839 (1991)). Summaries can be found in known textbooks of genetics and molecular biology, such as that by Hagemann ("Allgemeine Genetik [General Genetics]", Gustav Fischer Verlag, Stuttgart, 1986).

Mutations which come into consideration are transitions, transversions, insertions and deletions of at least one (1) base pair or nucleotide. Depending on the effect of the mutation-elicited amino acid substitution on the enzyme activity, reference is made to missense mutations or to nonsense mutations. A missense mutation leads to the replacement of a given amino acid in a protein with a different amino acid, with the amino acid replacement in particular being non-conservative. This thereby impairs the functional ability or activity of the protein and reduces it down to a value of from 0 to 75%, 0 to 50%, 0 to 25%, 0 to 10% or 0 to 5%. A nonsense mutation leads to a stop codon in the coding region of the gene and thus to premature termination of the translation. Insertions or deletions of at least one base pair in a gene lead to frame shift mutations which in turn result in incorrect amino acids being incorporated or in the translation being prematurely terminated. If a stop codon is formed in the coding region as a consequence of the mutation, this then also leads to translation being terminated prematurely. Deletions of at least one (1) or more codons typically also lead to complete loss of the enzyme activity.

Directions for generating these mutations belong to the prior art and can be obtained from known textbooks of genetics and molecular biology such as the textbook by Knippers ("Molekulare Genetik [Molecular Genetics]", 6th edition, Georg Thieme Verlag, Stuttgart, Germany, 1995), that by Winnacker "Gene and Klone, [Genes and Clones]", VHC Verlagsgesellschaft, Weinheim, Germany, 1990) or that by Hagemann ("Allgemeine Genetik [General Genetics]", Gustav Fischer Verlag, Stuttgart, 1986).

Suitable mutations in the genes can be incorporated into suitable strains by means of gene or allele exchange. A customary method is the method, described by Hamilton et al. (Journal of Bacteriology 171: 4617-4622 (1989)), of gene exchange using a conditionally replicating pSC101 derivative pMAK705. Other methods described in the prior art, such as that of Martinez-Morales et al. (Journal of Bacteriology 181: 7143-7148 (1999)) or that of Boyd et al. (Journal of Bacteriology 182: 842-847 (2000)), can also be used.

It is likewise possible to transfer mutations in the relevant genes, or mutations which effect the expression of the relevant genes or open reading frames, into different strains by means of conjugation or transduction.

Furthermore, for the purpose of producing L-amino acids, in particular L-threonine, it can be advantageous, in addition to enhancing the open reading frame yjcG, to eliminate undesirable side-reactions (Nakayama: "Breeding of Amino Acid Producing Microorganisms", in: Overproduction of Microbial Products, Krumphanzl, Sikyta, Vanek (eds.), Academic Press, London, UK, 1982).

The performance of the isolated bacteria, or of the fermentation process using these bacteria, is improved, with regard to one or more of the parameters selected from the group consisting of the product concentration (product per volume), the product yield (product formed per carbon source consumed) and the product formation (product formed per volume and time), or else other process parameters and combinations thereof, by at least 0.5%, at least 1%, at least 1.5% or at least 2%, based on the nonrecombinant microorganism or parent strain, or the fermentation process using this microorganism or parent strain.

The microorganisms which are prepared in accordance with the invention can be cultured in a batch process, in a fed-batch process, in a repeated fed-batch process or in a continuous process (DE102004028859.3 or U.S. Pat. No. 5,763,230). Known culturing methods are summarized in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral installations] (Vieweg Verlag, Brunswick/Wiesbaden, 1994)).

The culture medium to be used must satisfy the demands of the given strains in an appropriate manner. The American Society for Bacteriology manual "Manual of Methods for General Bacteriology" (Washington D.C., USA, 1981) contains descriptions of media for culturing a variety of microorganisms.

Sugars and carbohydrates, such as glucose, sucrose, lactose, fructose, maltose, molasses, starch and, where appropriate, cellulose, oils and fats, such as soybean oil, sunflower oil, peanut oil and coconut fat, fatty acids, such as palmitic acid, stearic acid and linoleic acid, alcohols, such as glycerol and ethanol, and organic acids, such as acetic acid, may be used as the carbon source. These substances may be used individually or as a mixture. For example, mixtures of glucose and fructose can be used in a ratio of approx. 1:1, as described in EP 1 225 230.

Organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate, may be used as the nitrogen source. The nitrogen sources may be used individually or as a mixture.

Phosphoric acid, potassium dihydrogen phosphate or dipotassium hydrogen phosphate, or the corresponding sodium-containing salts, may be used as the phosphorus source. In addition, the culture medium must contain salts of metals, such as magnesium sulfate or iron sulfate, which are required for growth. Finally, essential growth promoters, such as amino acids and vitamins, may be used in addition to the abovementioned substances. Suitable precursors can also be added to the culture medium. Said ingredients may be added to the culture in the form of a one-off mixture or suitably fed in during the culture.

The fermentation is generally carried out at a pH of from 5.5 to 9.0, in particular of from 6.0 to 8.0. Basic compounds, such as sodium hydroxide, potassium hydroxide, ammonia or ammonia water, or acidic compounds, such as phosphoric acid or sulfuric acid, are used in a suitable manner for controlling the pH of the culture. Antifoamants, such as fatty acid polyglycol esters, can be used for controlling foaming. Suitable selectively acting substances, for example antibiotics, can be added to the medium in order to maintain the stability of plasmids. Oxygen or oxygen-containing gas mixtures, such as air, are passed into the culture in order to maintain aerobic conditions. The temperature of the culture is normally from 25° C. to 45° C. and preferably from 30° C. to 40° C. The action of the microorganisms results in the L-amino acid being accumulated in the culture broth. The culture is continued until a maximum of L-amino acids or L-threonine has been formed. This objective is normally reached within 10 to 160 hours.

The L-amino acids can be isolated, collected or concentrated from the culture broth, which has been taken off, and then purified, where appropriate. Ion exchange chromatography and crystallization are typical methods for purifying the L-amino acids. These methods result in L-amino acids which are to a large extent pure.

It is likewise possible to prepare a product from the culture broth (=fermentation broth), which has been taken off, by removing the biomass of the bacterium, which is present in the culture broth, completely (100%) or almost completely, i.e. more than or greater than (>) 90%, and to a large extent, i.e. to an extent of 30%-100%, preferably greater than or equal to (≥) 50%, ≥70% or ≥90%, or else completely (100%), leaving the remaining constituents of the fermentation broth in the product.

Separation methods such as centrifugation, filtration, decantation or flocculation, or a combination thereof, are used for removing or separating off the biomass.

The resulting broth is then inspissated or concentrated using known methods, for example using a rotary evaporator, a thin film evaporator or a falling film evaporator, by means of reverse osmosis or by means of nanofiltration, or a combination of these methods.

This concentrated broth is then worked-up into what is preferably a flowable, finely divided powder using the methods of freeze drying, spray drying or spray granulation, or using other methods. This flowable, finely divided powder can then in turn be converted into a coarse-grain, readily flowable, storable, and to a large extent dust-free, product using suitable compacting or granulating methods. A total of more than 90% of the water is removed in this connection, such that the water content in the product is less than 10%, less than 5% or less than 3%.

L-amino acids can be analyzed by means of anion exchange chromatography followed by derivatization with ninhydrin, as described in Spackman et al. (Analytical Chemistry 30: 1190-1206 (1958)), or by means of reversed phase HPLC, so as described in Lindroth et al. (Analytical Chemistry 51: 1167-1174 (1979)).

The process according to the invention can be used for fermentatively preparing L-amino acids, such as L-threonine, L-isoleucine, L-valine, L-methionine, L-homoserine, L-tryptophan and L-lysine, in particular L-threonine.

The present invention is explained in more detail below with the aid of implementation examples.

Minimal (M9) and complete (LB) media used for *Escherichia coli* are described by J. H. Miller (A short course in bacterial genetics (1992), Cold Spring Harbor Laboratory Press). The isolation of plasmid DNA from *Escherichia coli*, and also all techniques for restricting, ligating and treating with Klenow phosphatase and alkali phosphatase, are carried out as described in Sambrook et al. (Molecular Cloning—A Laboratory Manual (1989) Cold Spring Harbor Laboratory Press). Unless otherwise indicated, *Escherichia coli* are transformed as described in Chung et al. (Proceedings of the National Academy of Sciences of the United States of America 86: 2172-2175 (1989)).

The incubation temperature when preparing strains and transformants is 37° C.

Example 1

Constructing the Expression Plasmid pMW218yjcG

The *E. coli* K12 yjcG-ORF is amplified using the polymerase chain reaction (PCR) and synthetic oligonucleotides. PCR primers are synthesized (MWG Biotech, Ebersberg, Deutschland) on the basis of the nucleotide sequence of the yjcG gene in *E. coli* K12 MG1655 (Accession Number NC000913 (Region 4281276-4282925), Blattner et al. (Science 277: 1453-1474 (1997)). The sequences of the primers are modified so as to form recognition sites for restriction enzymes. The HindIII recognition sequence is selected for the yjcG-1 primer and the SacI recognition sequence is selected for the yjcG-2 primer, with these sequences being underlined in the nucleotide sequences shown below:

```
yjcG-1:
                                          (SEQ ID No. 7)
5'-GATCAAGCTTATCCGGCCTACATTCG-3' yjcg-2:
                                          (SEQ ID No. 8)
5'-GATCTAGAGCTCGATTAATGCGCGCGGCCTT-3'
```

The *E. coli* K12 MG1655 chromosomal DNA used for the PCR is isolated using "Qiagen Genomic-tips 100/G" (QIAGEN, Hilden, Germany) in accordance with the manufacturer's instructions. A DNA fragment of approx. 2084 bp in size (SEQ ID No. 9) can be amplified under standard PCR conditions (Innis et al. (1990) PCR Protocols. A Guide to Methods and Applications, Academic Press) using Vent DNA polymerase (New England Biolaps GmbH, Frankfurt, Germany) and the specific primers.

The amplified yjcG fragment is ligated to the vector pCR-Blunt II-TOPO (Zero TOPO TA Cloning Kit, Invitrogen, Groningen, Netherlands) in accordance with the manufacturer's instructions and transformed into the *E. coli* strain TOP10. Plasmid-harboring cells are selected on LB Agar containing 50 µg of kanamycin/ml. After the plasmid DNA has been isolated, the vector is cleaved with the enzymes PvuI and HindIII/SacI and, after the cleavage has been checked in a 0.8% agarose gel, designated pCRBluntyjcG.

The vector pCRBluntyjcG is then cleaved with the enzymes HindIII and SacI and the yjcG fragment is separated in a 0.8% agarose gel; it is then isolated from the gel (QIAquick Gel Extraction Kit, QIAGEN, Hilden, Germany) and ligated to the low-copy vector pMW218 (Nippon Gene, Toyama, Japan) which has been digested with the enzymes HindIII and SacI. The *E. coli* strain DH5α (Grant et al.; Proceedings of the National Academy of Sciences USA, 87 (1990) 4645-4649) is transformed with the ligation mixture and plasmid-harboring cells are selected on LB agar containing 50 µg of kanamycin/ml.

The fact that cloning has been successful can be demonstrated, after the plasmid DNA has been isolated, by performing a control cleavage using the enzymes EcoRI/SalI.

The plasmid is designated pMW218yjcG (FIG. 1).

Example 2

Preparing L-Threonine Using the Strain MG442/pMW218yjcG

The L-threonine-producing *E. coli* strain MG442 is described in the patent specification U.S. Pat. No. 4,278,765 and is deposited in the Russian national collection of industrial microorganisms (VKPM, Moscow, Russia) as CMIM B-1628.

The strain MG442 is transformed with the expression plasmid pMW218yjcG described in example 1, and with the vector pMW218, and plasmid-harboring cells are selected on LB agar containing 50 µg of kanamycin/ml. This results in the strains MG442/pMW218yjcG and MG442/pMW218. Selected individual colonies are then propagated further on minimal medium having the following composition: 3.5 g of $Na_2HPO_4*2H_2O$/l, 1.5 g of $KH_2PO_4$/l, 1 g of $NH_4Cl$/l, 0.1 g of $MgSO_4*7H_2O$/l, 2 g of glucose/l, 20 g of agar/l, 50 mg of kanamycin/l. The formation of L-threonine is checked in 10 ml batch cultures which are contained in 100 ml Erlenmeyer flasks. For this, a 10 ml preculture medium of the following composition: 2 g of yeast extract/l, 10 g of $(NH_4)_2SO_4$/l, 1 g of $KH_2PO_4$/l, 0.5 g of $MgSO_4*7H_2O$/l, 15 g of $CaCO_3$/l, 20 g of glucose/l, 50 mg of kanamycin/l, is inoculated and incubated, at 37° C. and 180 rpm for 16 hours, on a Kühner AG ESR incubator (Birsfelden, Switzerland). In each case 250 µl of this preliminary culture are inoculated over into 10 ml of production medium (25 g of $(NH_4)_2SO_4$/l, 2 g of $KH_2PO_4$/l, 1 g of $MgSO_4*7H_2O$/l, 0.03 g of $FeSO_4*7H_2O$/l, 0.018 g of $MnSO_4*1H_2O$/l, 30 g of $CaCO_3$/l, 20 g of glucose/l, 50 mg of kanamycin/l) and incubated at 37° C. for 48 hours. After the incubation, the optical density (OD) of the culture suspension is determined at a measurement wavelength of 660 nm using a Dr. Lange LP2W photometer (Düsseldorf, Germany).

An Eppendorf-BioTronik amino acid analyzer (Hamburg, Germany) is then used to determine, by means of ion exchange chromatography and post-column reaction involving ninhydrin detection, the concentration of the resulting L-threonine in the culture supernatant, which has been sterilized by filtration.

The result of the experiment is shown in table 1.

TABLE 1

| Strain | OD (660 nm) | L-Threonin g/l |
|---|---|---|
| MG442/pMW218 | 6.4 | 2.15 |
| MG442/pMW218yjcG | 5.5 | 2.5 |

BRIEF DESCRIPTION OF THE FIGURE

FIG. 1: Map of the yjcG gene-containing plasmid MW218yjcG

Length specifications are to be regarded as approximate. The abbreviations and designations employed have the following meanings:
  kan: gene which encodes resistance to kanamycin
  yjcG: coding region of the yjcG gene
  lacZ': gene fragment which encodes the α-peptide of β-galactosidase The abbreviations for the restriction enzymes have the following meaning:
  EcoRI: restriction endonuclease from *Escherichia coli*
  HindIII: restriction endonuclease from *Haemophilus influenzae*
  SacI: restriction endonuclease from *Streptomyces achromogenes*
  SalI: restriction endonuclease from *Streptomyces albus*

The invention claimed is:

1. A process for preparing a desired L-amino acid by fermenting a recombinant microorganism of the Enterobacteriaceae family, which comprises:
   a) culturing the recombinant microorganism, which has been genetically modified to overexpress a polynucleotide encoding a polypeptide having acetate permease activity and an amino acid sequence that is at least 95% identical to SEQ ID NO: 2, in a fermentation medium under conditions under which the desired L-amino acid accumulates in the fermentation medium or in the recombinant microorganism, wherein the copy number of the polynucleotide encoding the polypeptide having acetate permease activity has been increased by at least 1 and/or a strong promoter is operably linked to the polynucleotide encoding the polypeptide having acetate permease activity; and
   b) concentrating the fermentation medium prior to recovery of the desired L-amino acid.

2. The process as claimed in claim 1, wherein the desired L-amino acid is L-threonine and the recombinant microorganism has been further modified by transforming it with one or more polynucleotides selected from the group consisting of:
   a) at least one gene of the thrABC operon encoding aspartate kinase, homoserine dehydrogenase, homoserine kinase and threonine synthase,
   b) a gene encoding pyruvate carboxylase (pyc),
   c) a gene encoding phosphoenolpyruvate synthase (pps),
   d) a gene encoding phosphoenolpyruvate carboxylase (ppc),
   e) genes encoding the subunits of pyridine transhydrogenase (pntA and pntB),
   f) a gene encoding a threonine resistance-mediating protein (thtC),
   g) a gene encoding a threonine export carrier (thrE),
   h) a gene encoding glutamate dehydrogenase (gdhA),
   i) a gene encoding phosphohistidine protein hexose phosphotransferase (ptsH),
   j) a gene encoding enzyme I of the phosphotransferase system (ptsI),
   k) a gene encoding glucose-specific IIA component (crr),
   l) a gene encoding glucose-specific IIBC component (ptsG),
   m) a gene encoding cysteine synthase A (cysK),
   n) a gene encoding a regulator of the cys regulon (cysB),
   o) a gene encoding NADPH sulfite reductase flavoprotein (cysJ),
   p) a gene encoding NADPH sulfite reductase hemoprotein (cysI),
   q) a gene encoding adenylyl sulfate reductase (cysH),
   r) a gene encoding the decarboxylase subunit of 2-ketoglutarate dehydrogenase (sucA),
   s) a gene encoding the dihydrolipoyl-transsuccinase E2 subunit of 2-ketoglutarate dehydrogenase (sucB),
   t) a gene encoding the β-subunit of succinyl-CoA synthetase (sucC),
   u) a gene encoding the α-subunit of succinyl-CoA synthetase (sucD),
   v) *Escherichia coli* yibD open reading frame (ORF), and
   w) a gene encoding acetyl-coenzyme A synthetase (acs).

3. The process as claimed in claim, 1, wherein the metabolic pathways which reduce the formation of the desired L-amino acid are at least partially attenuated in the recombinant microorganism by disrupting one or more endogenous polynucleotides selected from the group consisting of:
   a) a gene encoding threonine dehydrogenase (tdh),
   b) a gene encoding malate dehydrogenase (mdh),
   c) *Escherichia coli* yjfA open reading frame (ORF),
   d) *Escherichia coli* ytfP open reading frame (ORF),
   e) a gene encoding phosphoenolpyruvate carboxykinase (pckA),
   f) a gene encoding pyruvate oxidase (poxB),
   g) a gene encoding the DgsA regulator of the phosphotransferase system (dgsA),
   h) a gene encoding fructose repressor (fruR),
   i) a gene encoding sigma$^{38}$ factor (rpoS), and
   j) a gene encoding aspartate ammonium lyase (aspA).

4. The process as claimed in claim 3, wherein the desired L-amino acid is L-threonine.

5. The process as claimed in claim 1, wherein the desired L-amino acid is selected from the group consisting of L-asparagine, L-serine, L-glutamate, L-glycine, alanine, L-cysteine, L-valine, L-methionine, L-proline, L-isoleucine, L-leucine, L-tyrosine, L-phenylalanine, L-histidine, L-tryptophan, L-arginine, and L-homoserine.

6. The process as claimed in claim 1, wherein the desired L-amino acid is selected from the group L-isoleucine, L-valine, L-methionine, L-homoserine, L-tryptophan, and L-lysine.

7. The process of claim 1, wherein the overexpressed polynucleotide in the recombinant microorganism is selected from the group consisting of:
   a) a polynucleotide having a nucleotide sequence which is SEQ ID NO:1 or its full-length complement; and
   b) a polynucleotide which encodes a polypeptide having SEQ ID NO:2.

8. The process of claim 1, wherein the amino acid sequence is 100% identical to SEQ ID NO:2.

9. The process of claim 1, wherein the recombinant microorganism is genetically modified to contain: (i) a vector which contains the polynucleotide encoding the polypeptide having acetate permease activity, and/or (ii) a promoter which promotes the expression of the polynucleotide.

10. The process of claim 1, wherein the polynucleotide encoding the polypeptide having acetate permease activity is integrated into the chromosome of the microorganism.

11. The process of claim 9, wherein the vector replicates extrachromosomally.

12. The process of claim 1, wherein the recombinant microorganism comprises
   a) a mutated promoter and regulatory region or a mutated ribosomal binding site upstream of the polynucleotide encoding the polypeptide having acetate permease activity, or
   b) expression cassettes or promoters incorporated upstream of the polynucleotide encoding the polypeptide having acetate permease activity.

13. The process of claim 1, wherein the recombinant microorganism is capable of expressing the polynucleotide encoding the polypeptide having acetate permease activity by at least 10% more than the corresponding microorganism that has not been genetically modified to overexpress the polynucleotide encoding the polypeptide having acetate permease activity.

14. The process of claim 1, wherein the microorganism which was genetically modified to result in the recombinant microorganism is selected from the genera *Escherichia, Erwinia, Providencia* and *Serratia*.

15. The process of claim 1, wherein the recombinant organism comprises one or more additional genes of the pathway for the biosynthesis of the desired L-amino acid.

16. The process of claim 1, wherein the desired L-amino acid is L-threonine.

* * * * *

SEQUENCE LISTING

```
<160> NUMBER OF SEQ ID NOS: 10

<210> SEQ ID NO 1
<211> LENGTH: 1650
<212> TYPE: DNA
<213> ORGANISM: Escherichia coli
<220> FEATURE:
<221> NAME/KEY: CDS
<222> LOCATION: (1)..(1650)
<223> OTHER INFORMATION: yjcG coding region

<400> SEQUENCE: 1 atg aaa aga gtt ctg acg gcg ctt gcc gcc aca ctc cct ttc gca gct        48
Met Lys Arg Val Leu Thr Ala Leu Ala Ala Thr Leu Pro Phe Ala Ala
1               5                   10                  15 aac gcc gcg gat gct att agc ggg gcc gta gag cgc cag cca acg aac        96
Asn Ala Ala Asp Ala Ile Ser Gly Ala Val Glu Arg Gln Pro Thr Asn
                20                  25                  30 tgg cag gcg att att atg ttc ctg att ttc gtc gtg ttt acg ctc ggc       144
Trp Gln Ala Ile Ile Met Phe Leu Ile Phe Val Val Phe Thr Leu Gly
            35                  40                  45 att acc tac tgg gca tca aaa cgc gta cgt tct cgt agc gac tac tac       192
Ile Thr Tyr Trp Ala Ser Lys Arg Val Arg Ser Arg Ser Asp Tyr Tyr
        50                  55                  60 acc gca ggc ggc aat atc act ggc ttc cag aac ggg ctg gcg att gcc       240
Thr Ala Gly Gly Asn Ile Thr Gly Phe Gln Asn Gly Leu Ala Ile Ala
65                  70                  75                  80 ggg gac tat atg tcc gcc gcc tca ttc ttg ggg atc tcc gcg ctg gtg       288
Gly Asp Tyr Met Ser Ala Ala Ser Phe Leu Gly Ile Ser Ala Leu Val
                85                  90                  95 ttt acc tcc ggc tat gac ggc tta att tac tcg ctg ggc ttc ctg gtg       336
Phe Thr Ser Gly Tyr Asp Gly Leu Ile Tyr Ser Leu Gly Phe Leu Val
                100                 105                 110 ggc tgg ccg atc att ttg ttc ctg att gcc gaa cgt ctg cgt aac ctg       384
Gly Trp Pro Ile Ile Leu Phe Leu Ile Ala Glu Arg Leu Arg Asn Leu
            115                 120                 125 ggg cgc tac acc ttt gcc gat gtg gcc tct tac cgt ctg aaa caa ggg       432
Gly Arg Tyr Thr Phe Ala Asp Val Ala Ser Tyr Arg Leu Lys Gln Gly
        130                 135                 140 ccg att cgt att ctt tcg gcc tgt ggt tct ctg gtg gtg gtg gcg ctt       480
Pro Ile Arg Ile Leu Ser Ala Cys Gly Ser Leu Val Val Val Ala Leu
145                 150                 155                 160 tac ctt atc gcc cag atg gtg ggc gca ggt aaa ctg atc gag ctg ctg       528
Tyr Leu Ile Ala Gln Met Val Gly Ala Gly Lys Leu Ile Glu Leu Leu
                165                 170                 175 ttt ggc ctt aac tat cac att gcg gtg gtg ctg gtc ggc gtg ctg atg       576
Phe Gly Leu Asn Tyr His Ile Ala Val Val Leu Val Gly Val Leu Met
                180                 185                 190 atg atg tac gtc ctg ttc ggc ggc atg ctg gcg acc acc tgg gtg caa       624
Met Met Tyr Val Leu Phe Gly Gly Met Leu Ala Thr Thr Trp Val Gln
            195                 200                 205
```

```
att atc aaa gcc gtg ctg ttg ctg ttc ggt gcc agc ttt atg gcc ttt     672
Ile Ile Lys Ala Val Leu Leu Leu Phe Gly Ala Ser Phe Met Ala Phe
    210             215                 220 atg gtg atg aaa cac gtc ggc ttt agc ttc aac aat ctg ttc agt gaa     720
Met Val Met Lys His Val Gly Phe Ser Phe Asn Asn Leu Phe Ser Glu
225             230                 235                 240 gcg atg gcg gta cac ccg aaa ggt gtc gac atc atg aag ccg ggc ggg     768
Ala Met Ala Val His Pro Lys Gly Val Asp Ile Met Lys Pro Gly Gly
                245                 250                 255 ctg gtg aaa gat ccg atc tcc gcg ctc tct ctg ggt ctg gga ctg atg     816
Leu Val Lys Asp Pro Ile Ser Ala Leu Ser Leu Gly Leu Gly Leu Met
        260                 265                 270 ttt ggt acg gcg ggc ttg ccg cac att ctg atg cgc ttc ttt aca gtc     864
Phe Gly Thr Ala Gly Leu Pro His Ile Leu Met Arg Phe Phe Thr Val
            275                 280                 285 agc gat gcc cgc gaa gca cgt aag agc gtg ttc tac gcc acc ggg ttt     912
Ser Asp Ala Arg Glu Ala Arg Lys Ser Val Phe Tyr Ala Thr Gly Phe
        290                 295                 300 atg ggc tac ttc tat att ctg acc ttt att atc ggc ttc ggc gcg atc     960
Met Gly Tyr Phe Tyr Ile Leu Thr Phe Ile Ile Gly Phe Gly Ala Ile
305             310                 315                 320 atg ctg gtt ggt gcg aat ccg gaa tat aaa gac gcg gcg ggc cat ctg    1008
Met Leu Val Gly Ala Asn Pro Glu Tyr Lys Asp Ala Ala Gly His Leu
                325                 330                 335 att ggt ggt aac aac atg gcg gcc gtt cac ctg gcg aat gca gtg ggc    1056
Ile Gly Gly Asn Asn Met Ala Ala Val His Leu Ala Asn Ala Val Gly
        340                 345                 350 ggc aac ctg ttc ctc ggt ttt att tca gcg gtt gct ttc gcc act atc    1104
Gly Asn Leu Phe Leu Gly Phe Ile Ser Ala Val Ala Phe Ala Thr Ile
            355                 360                 365 ctc gcg gtg gtt gcg ggt ctg acg ctg gcg ggc gca tcc gcg gtt tcg    1152
Leu Ala Val Val Ala Gly Leu Thr Leu Ala Gly Ala Ser Ala Val Ser
        370                 375                 380 cat gac ttg tac gct aac gtc ttc aaa aaa ggc gcg acc gaa cgt gaa    1200
His Asp Leu Tyr Ala Asn Val Phe Lys Lys Gly Ala Thr Glu Arg Glu
385             390                 395                 400 gag ctg cgg gta tca aaa atc acc gta ctg atc ctc ggc gtg att gcg    1248
Glu Leu Arg Val Ser Lys Ile Thr Val Leu Ile Leu Gly Val Ile Ala
                405                 410                 415 att atc ctc ggc gtg ctg ttt gag aat cag aac atc gcc ttt atg gtg    1296
Ile Ile Leu Gly Val Leu Phe Glu Asn Gln Asn Ile Ala Phe Met Val
        420                 425                 430 ggg ctg gcg ttt gcc atc gcg gcg agc tgt aac ttc ccg atc att ctg    1344
Gly Leu Ala Phe Ala Ile Ala Ala Ser Cys Asn Phe Pro Ile Ile Leu
            435                 440                 445 ctt tct atg tac tgg tcg aaa ctg acc acg cgt ggc gcg atg atg ggt    1392
Leu Ser Met Tyr Trp Ser Lys Leu Thr Thr Arg Gly Ala Met Met Gly
        450                 455                 460 ggc tgg ctg ggg ctg att acc gca gta gta ctg atg atc ctc ggc ccg    1440
Gly Trp Leu Gly Leu Ile Thr Ala Val Val Leu Met Ile Leu Gly Pro
465             470                 475                 480 acg att tgg gta cag atc ctt ggt cac gaa aaa gcc atc ttc ccg tat    1488
Thr Ile Trp Val Gln Ile Leu Gly His Glu Lys Ala Ile Phe Pro Tyr
                485                 490                 495 gaa tac ccg gcg ctg ttc tct atc acc gtg gca ttc ctc ggc atc tgg    1536
Glu Tyr Pro Ala Leu Phe Ser Ile Thr Val Ala Phe Leu Gly Ile Trp
        500                 505                 510 ttc ttc tcg gca acc gat aac tca gcg gaa ggc gcg cgt gag cgt gaa    1584
Phe Phe Ser Ala Thr Asp Asn Ser Ala Glu Gly Ala Arg Glu Arg Glu
            515                 520                 525
```

```
ctg ttc cgc gcg cag ttt atc cgc tcc cag acc ggc ttt ggc gtt gag    1632
Leu Phe Arg Ala Gln Phe Ile Arg Ser Gln Thr Gly Phe Gly Val Glu
530                 535                 540 caa ggc cgc gcg cat taa                                            1650
Gln Gly Arg Ala His
545

<210> SEQ ID NO 2
<211> LENGTH: 549
<212> TYPE: PRT
<213> ORGANISM: Escherichia coli

<400> SEQUENCE: 2

Met Lys Arg Val Leu Thr Ala Leu Ala Thr Leu Pro Phe Ala Ala
1               5                   10                  15

Asn Ala Ala Asp Ala Ile Ser Gly Ala Val Glu Arg Gln Pro Thr Asn
                20                  25                  30

Trp Gln Ala Ile Ile Met Phe Leu Ile Phe Val Val Phe Thr Leu Gly
                35                  40                  45

Ile Thr Tyr Trp Ala Ser Lys Arg Val Arg Ser Arg Ser Asp Tyr Tyr
50                  55                  60

Thr Ala Gly Gly Asn Ile Thr Gly Phe Gln Asn Gly Leu Ala Ile Ala
65                  70                  75                  80

Gly Asp Tyr Met Ser Ala Ala Ser Phe Leu Gly Ile Ser Ala Leu Val
                    85                  90                  95

Phe Thr Ser Gly Tyr Asp Gly Leu Ile Tyr Ser Leu Gly Phe Leu Val
                100                 105                 110

Gly Trp Pro Ile Ile Leu Phe Leu Ile Ala Glu Arg Leu Arg Asn Leu
                115                 120                 125

Gly Arg Tyr Thr Phe Ala Asp Val Ala Ser Tyr Arg Leu Lys Gln Gly
130                 135                 140

Pro Ile Arg Ile Leu Ser Ala Cys Gly Ser Leu Val Val Val Ala Leu
145                 150                 155                 160

Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
                180                 185                 190

Met Met Tyr Val Leu Phe Gly Gly Met Leu Ala Thr Thr Trp Val Gln
                195                 200                 205

Ile Ile Lys Ala Val Leu Leu Leu Phe Gly Ala Ser Phe Met Ala Phe
210                 215                 220

Met Val Met Lys His Val Gly Phe Ser Phe Asn Asn Leu Phe Ser Glu
225                 230                 235                 240

Ala Met Ala Val His Pro Lys Gly Val Asp Ile Met Lys Pro Gly Gly
                245                 250                 255

Leu Val Lys Asp Pro Ile Ser Ala Leu Ser Leu Gly Leu Gly Leu Met
                260                 265                 270

Phe Gly Thr Ala Gly Leu Pro His Ile Leu Met Arg Phe Phe Thr Val
                275                 280                 285

Ser Asp Ala Arg Glu Ala Arg Lys Ser Val Phe Tyr Ala Thr Gly Phe
290                 295                 300

Met Gly Tyr Phe Tyr Ile Leu Thr Phe Ile Ile Gly Phe Gly Ala Ile
305                 310                 315                 320

Met Leu Val Gly Ala Asn Pro Glu Tyr Lys Asp Ala Ala Gly His Leu
                325                 330                 335
```

-continued

```
Ile Gly Gly Asn Asn Met Ala Ala Val His Leu Ala Asn Ala Val Gly
                340                 345                 350

Gly Asn Leu Phe Leu Gly Phe Ile Ser Ala Val Ala Phe Ala Thr Ile
            355                 360                 365

Leu Ala Val Val Ala Gly Leu Thr Leu Ala Gly Ala Ser Ala Val Ser
        370                 375                 380

His Asp Leu Tyr Ala Asn Val Phe Lys Lys Gly Ala Thr Glu Arg Glu
385                 390                 395                 400

Glu Leu Arg Val Ser Lys Ile Thr Val Leu Ile Leu Gly Val Ile Ala
                405                 410                 415

Ile Ile Leu Gly Val Leu Phe Glu Asn Gln Asn Ile Ala Phe Met Val
            420                 425                 430

Gly Leu Ala Phe Ala Ile Ala Ala Ser Cys Asn Phe Pro Ile Ile Leu
        435                 440                 445

Leu Ser Met Tyr Trp Ser Lys Leu Thr Thr Arg Gly Ala Met Met Gly
    450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Thr Val Ala Phe Leu Gly Ile Trp
            500                 505                 510

Phe Phe Ser Ala Thr Asp Asn Ser Ala Glu Gly Ala Arg Glu Arg Glu
        515                 520                 525

Leu Phe Arg Ala Gln Phe Ile Arg Ser Gln Thr Gly Phe Gly Val Glu
    530                 535                 540

Gln Gly Arg Ala His
545
```

<210> SEQ ID NO 3
<211> LENGTH: 1650
<212> TYPE: DNA
<213> ORGANISM: Salmonella typhimurium
<220> FEATURE:
<221> NAME/KEY: CDS
<222> LOCATION: (1)..(1650)
<223> OTHER INFORMATION: yjcG coding region

<400> SEQUENCE: 3

```
atg aag aga gtt ctg acg gcg ctt gcc gcc gca ctc ccc ttc gcc gct    48
Met Lys Arg Val Leu Thr Ala Leu Ala Ala Ala Leu Pro Phe Ala Ala
1               5                   10                  15 cat gcg gcg gat gcc att agc ggc gcg gtt gaa cgc cag ccc acc aac    96
His Ala Ala Asp Ala Ile Ser Gly Ala Val Glu Arg Gln Pro Thr Asn
            20                  25                  30 tgg cag gcg att atc atg ttt ttg att ttc gtc gtg ttt acg ctc ggt   144
Trp Gln Ala Ile Ile Met Phe Leu Ile Phe Val Val Phe Thr Leu Gly
        35                  40                  45 att acc tac tgg gcc tct aaa cgc gta cgt tcc cgt agc gac tac tac   192
Ile Thr Tyr Trp Ala Ser Lys Arg Val Arg Ser Arg Ser Asp Tyr Tyr
    50                  55                  60 acc gct ggc ggc aat atc acc ggg ttc cag aac ggc ctg gcg att gcc   240
Thr Ala Gly Gly Asn Ile Thr Gly Phe Gln Asn Gly Leu Ala Ile Ala
65                  70                  75                  80 ggc gac tat atg tct gcc gcg tca ttt ctc ggc att tcc gcg ctg gtg   288
Gly Asp Tyr Met Ser Ala Ala Ser Phe Leu Gly Ile Ser Ala Leu Val
                85                  90                  95
```

| | | |
|---|---|---|
| ttt acc tcc ggt tat gac ggg ctg atc tat tcg ctg ggc ttc ctt gtc<br>Phe Thr Ser Gly Tyr Asp Gly Leu Ile Tyr Ser Leu Gly Phe Leu Val<br>100                           105                          110 | 336 |
| ggc tgg cca atc atc ctg ttt ttg att gcc gag cgc ctg cgt aat ctg<br>Gly Trp Pro Ile Ile Leu Phe Leu Ile Ala Glu Arg Leu Arg Asn Leu<br>115                          120                          125 | 384 |
| gga cgt tat act ttt gct gac gtt gcc tct tat cgc ctg aaa cag ggg<br>Gly Arg Tyr Thr Phe Ala Asp Val Ala Ser Tyr Arg Leu Lys Gln Gly<br>130                          135                          140 | 432 |
| cca atc cgt att ctt tcg gcc tgt ggc tcc ctg gta gtg gtg gcg ctt<br>Pro Ile Arg Ile Leu Ser Ala Cys Gly Ser Leu Val Val Val Ala Leu<br>145                          150                          155                          160 | 480 |
| tat ctc atc gcc caa atg gtc ggc gcc ggt aaa ctg att gaa ctg ctg<br>Tyr Leu Ile Ala Gln Met Val Gly Ala Gly Lys Leu Ile Glu Leu Leu<br>                         165                          170                          175 | 528 |
| ttc ggc ctc aac tat cac atc gct gtg gtg ctg gtc ggc gtg ctg atg<br>Phe Gly Leu Asn Tyr His Ile Ala Val Val Leu Val Gly Val Leu Met<br>                         180                          185                          190 | 576 |
| atg atg tac gtg ctg ttc ggc ggg atg ctg gcg aca acg tgg gtg caa<br>Met Met Tyr Val Leu Phe Gly Gly Met Leu Ala Thr Thr Trp Val Gln<br>                         195                          200                          205 | 624 |
| att atc aaa gcc gtc ctg ttg ctg ttt ggc gcc agt ttt atg gcc ttt<br>Ile Ile Lys Ala Val Leu Leu Leu Phe Gly Ala Ser Phe Met Ala Phe<br>210                          215                          220 | 672 |
| atg gtg atg aaa cac gtc ggc ttt agc ttc aat aat ctg ttt acc gaa<br>Met Val Met Lys His Val Gly Phe Ser Phe Asn Asn Leu Phe Thr Glu<br>225                          230                          235                          240 | 720 |
| gcc atg gcg gta cac ccg aaa ggc acg gcg att atg agc cca gga gga<br>Ala Met Ala Val His Pro Lys Gly Thr Ala Ile Met Ser Pro Gly Gly<br>                         245                          250                          255 | 768 |
| ttg gtg caa gat ccg att tcg gca ttg tcg ttg ggt ctg gga ctg atg<br>Leu Val Gln Asp Pro Ile Ser Ala Leu Ser Leu Gly Leu Gly Leu Met<br>                         260                          265                          270 | 816 |
| ttc ggc acc gcc ggc ttg ccg cat att ctg atg cgt ttc ttt acg gtc<br>Phe Gly Thr Ala Gly Leu Pro His Ile Leu Met Arg Phe Phe Thr Val<br>275                          280                          285 | 864 |
| agc gat gcc cgc gaa gcg cgc aag agc gtg ttc tac gcc acc ggt ttt<br>Ser Asp Ala Arg Glu Ala Arg Lys Ser Val Phe Tyr Ala Thr Gly Phe<br>290                          295                          300 | 912 |
| atg ggc tat ttc tac att ctg acc ttt att atc ggc ttc ggc gct atc<br>Met Gly Tyr Phe Tyr Ile Leu Thr Phe Ile Ile Gly Phe Gly Ala Ile<br>305                          310                          315                          320 | 960 |
| atg ctg gtg ggg gcg aat ccc gcc tat aaa gat gcc gca ggc gcg ctg<br>Met Leu Val Gly Ala Asn Pro Ala Tyr Lys Asp Ala Ala Gly Ala Leu<br>                         325                          330                          335 | 1008 |
| att ggc ggc aat aac atg gcg gcg gtg cat ctg gcc aac gcg gta ggc<br>Ile Gly Gly Asn Asn Met Ala Ala Val His Leu Ala Asn Ala Val Gly<br>                         340                          345                          350 | 1056 |
| ggc aac ctg ttc ctc ggc ttt att tcg gca gtg gcg ttt gcc acc att<br>Gly Asn Leu Phe Leu Gly Phe Ile Ser Ala Val Ala Phe Ala Thr Ile<br>                         355                          360                          365 | 1104 |
| ctg gcg gtg gtc gca ggt ctg acg ctg gcg ggc gca tcg gcg gtg tcg<br>Leu Ala Val Val Ala Gly Leu Thr Leu Ala Gly Ala Ser Ala Val Ser<br>370                          375                          380 | 1152 |
| cat gac ttg tac gcc aac gtg ttc cgc aaa ggc gca acc gaa cgt gaa<br>His Asp Leu Tyr Ala Asn Val Phe Arg Lys Gly Ala Thr Glu Arg Glu<br>385                          390                          395                          400 | 1200 |
| gag ctg aag gtg tcg aaa atc acc gtc ctg gtg ctg ggc gtg atc gcc<br>Glu Leu Lys Val Ser Lys Ile Thr Val Leu Val Leu Gly Val Ile Ala<br>                         405                          410                          415 | 1248 |

```
att atc ctc ggc gtg ctg ttt gaa aat cag aac atc gcc ttt atg gtg    1296
Ile Ile Leu Gly Val Leu Phe Glu Asn Gln Asn Ile Ala Phe Met Val
            420                 425                 430 ggc ctg gca ttt gct atc gcc gcg agc tgc aac ttc ccc atc att ctg    1344
Gly Leu Ala Phe Ala Ile Ala Ala Ser Cys Asn Phe Pro Ile Ile Leu
        435                 440                 445 ctt tcc atg tac tgg tca aaa ctg acc acg cgc ggc gct atg ctg ggc    1392
Leu Ser Met Tyr Trp Ser Lys Leu Thr Thr Arg Gly Ala Met Leu Gly
    450                 455                 460 ggc tgg tta ggt tta ctg aca gcg gtg gtg ctg atg att ctt ggc cct    1440
Gly Trp Leu Gly Leu Leu Thr Ala Val Val Leu Met Ile Leu Gly Pro
465                 470                 475                 480 acc att tgg gtg cag atc ctc ggc cac gaa aaa gcg atc ttc ccg tat    1488
Thr Ile Trp Val Gln Ile Leu Gly His Glu Lys Ala Ile Phe Pro Tyr
                485                 490                 495 gag tat ccg gcg ctg ttc tct atc agc gtg gcg ttc ctg ggg atc tgg    1536
Glu Tyr Pro Ala Leu Phe Ser Ile Ser Val Ala Phe Leu Gly Ile Trp
            500                 505                 510 ttc ttc tcg gcc acc gat aac tcg gca gaa ggc aac cgt gaa cgt gag    1584
Phe Phe Ser Ala Thr Asp Asn Ser Ala Glu Gly Asn Arg Glu Arg Glu
        515                 520                 525 cag ttc cgc gct cag ttt atc cgc tcc caa acg gga ttc ggc gta caa    1632
Gln Phe Arg Ala Gln Phe Ile Arg Ser Gln Thr Gly Phe Gly Val Gln
    530                 535                 540 caa ggg cgt gcg cat taa                                            1650
Gln Gly Arg Ala His
545

<210> SEQ ID NO 4
<211> LENGTH: 549
<212> TYPE: PRT
<213> ORGANISM: Salmonella typhimurium

<400> SEQUENCE: 4

Met Lys Arg Val Leu Thr Ala Leu Ala Ala Leu Pro Phe Ala Ala
1               5                   10                  15

His Ala Ala Asp Ala Ile Ser Gly Ala Val Glu Arg Gln Pro Thr Asn
            20                  25                  30

Trp Gln Ala Ile Ile Met Phe Leu Ile Phe Val Val Phe Thr Leu Gly
        35                  40                  45

Ile Thr Tyr Trp Ala Ser Lys Arg Val Arg Ser Arg Ser Asp Tyr Tyr
    50                  55                  60

Thr Ala Gly Gly Asn Ile Thr Gly Phe Gln Asn Gly Leu Ala Ile Ala
65                  70                  75                  80

Gly Asp Tyr Met Ser Ala Ala Ser Phe Leu Gly Ile Ser Ala Leu Val
                85                  90                  95

Phe Thr Ser Gly Tyr Asp Gly Leu Ile Tyr Ser Leu Gly Phe Leu Val
            100                 105                 110

Gly Trp Pro Ile Ile Leu Phe Leu Ile Ala Glu Arg Leu Arg Asn Leu
        115                 120                 125

Gly Arg Tyr Thr Phe Ala Asp Val Ala Ser Tyr Arg Leu Lys Gln Gly
    130                 135                 140

Pro Ile Arg Ile Leu Ser Ala Cys Gly Ser Leu Val Val Ala Leu
145                 150                 155                 160

Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
            180                 185                 190
```

```
Met Met Tyr Val Leu Phe Gly Met Leu Ala Thr Thr Trp Val Gln
        195                 200                 205

Ile Ile Lys Ala Val Leu Leu Leu Phe Gly Ala Ser Phe Met Ala Phe
    210                 215                 220

Met Val Met Lys His Val Gly Phe Ser Phe Asn Asn Leu Phe Thr Glu
225                 230                 235                 240

Ala Met Ala Val His Pro Lys Gly Thr Ala Ile Met Ser Pro Gly Gly
                245                 250                 255

Leu Val Gln Asp Pro Ile Ser Ala Leu Ser Leu Gly Leu Gly Leu Met
            260                 265                 270

Phe Gly Thr Ala Gly Leu Pro His Ile Leu Met Arg Phe Phe Thr Val
        275                 280                 285

Ser Asp Ala Arg Glu Ala Arg Lys Ser Val Phe Tyr Ala Thr Gly Phe
    290                 295                 300

Met Gly Tyr Phe Tyr Ile Leu Thr Phe Ile Ile Gly Phe Gly Ala Ile
305                 310                 315                 320

Met Leu Val Gly Ala Asn Pro Ala Tyr Lys Asp Ala Gly Ala Leu
                325                 330                 335

Ile Gly Gly Asn Asn Met Ala Ala Val His Leu Ala Asn Ala Val Gly
            340                 345                 350

Gly Asn Leu Phe Leu Gly Phe Ile Ser Ala Val Ala Phe Ala Thr Ile
        355                 360                 365

Leu Ala Val Val Ala Gly Leu Thr Leu Ala Gly Ala Ser Ala Val Ser
    370                 375                 380

His Asp Leu Tyr Ala Asn Val Phe Arg Lys Gly Ala Thr Glu Arg Glu
385                 390                 395                 400

Glu Leu Lys Val Ser Lys Ile Thr Val Leu Val Leu Gly Val Ile Ala
                405                 410                 415

Ile Ile Leu Gly Val Leu Phe Glu Asn Gln Asn Ile Ala Phe Met Val
            420                 425                 430

Gly Leu Ala Phe Ala Ile Ala Ala Ser Cys Asn Phe Pro Ile Ile Leu
        435                 440                 445

Leu Ser Met Tyr Trp Ser Lys Leu Thr Thr Arg Gly Ala Met Leu Gly
    450                 455                 460

Gly Trp Leu Gly Leu Leu Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Ser Val Ala Phe Leu Gly Ile Trp
            500                 505                 510

Phe Phe Ser Ala Thr Asp Asn Ser Ala Glu Gly Asn Arg Glu Arg Glu
        515                 520                 525

Gln Phe Arg Ala Gln Phe Ile Arg Ser Gln Thr Gly Phe Gly Val Gln
    530                 535                 540

Gln Gly Arg Ala His
545

<210> SEQ ID NO 5
<211> LENGTH: 1650
<212> TYPE: DNA
<213> ORGANISM: Shigella flexneri
<220> FEATURE:
<221> NAME/KEY: CDS
<222> LOCATION: (1)..(1650)
<223> OTHER INFORMATION: yjcG coding region
```

<400> SEQUENCE: 5

```
atg aaa aga gtt ctg acg gcg ctt gcc gcc aca ctc cct ttc gca gct        48
Met Lys Arg Val Leu Thr Ala Leu Ala Ala Thr Leu Pro Phe Ala Ala
1               5                   10                  15 aac gcc gcg gat gct att agc ggg gcc gta gag cgc cag cca acg aac        96
Asn Ala Ala Asp Ala Ile Ser Gly Ala Val Glu Arg Gln Pro Thr Asn
                20                  25                  30 tgg cag gcg att att atg ttc ctg att ttc gtc gtg ttt acg ctc ggc       144
Trp Gln Ala Ile Ile Met Phe Leu Ile Phe Val Val Phe Thr Leu Gly
            35                  40                  45 att acc tac tgg gca tca aaa cgc gta cgt tct cgt agc gac tac tac       192
Ile Thr Tyr Trp Ala Ser Lys Arg Val Arg Ser Arg Ser Asp Tyr Tyr
        50                  55                  60 acc gca ggc ggc aat atc act ggc ttc cag aac ggg ctg gcg att gcc       240
Thr Ala Gly Gly Asn Ile Thr Gly Phe Gln Asn Gly Leu Ala Ile Ala
65                  70                  75                  80 ggg gac tat atg tcc gcc gcc tca ttc ttg ggg atc tcc gcg ctg gtg       288
Gly Asp Tyr Met Ser Ala Ala Ser Phe Leu Gly Ile Ser Ala Leu Val
                85                  90                  95 ttt acc tcc ggc tat gac ggg ctg atc tac tcg ttg ggc ttc ctg gtg       336
Phe Thr Ser Gly Tyr Asp Gly Leu Ile Tyr Ser Leu Gly Phe Leu Val
                100                 105                 110 ggc tgg cca atc att ctg ttt ctg att gcc gaa cgt ctg cgt aac ctg       384
Gly Trp Pro Ile Ile Leu Phe Leu Ile Ala Glu Arg Leu Arg Asn Leu
            115                 120                 125 gga cgc tac acc tct gcc gat gtg gcc tct tat cgt ctg aaa caa ggg       432
Gly Arg Tyr Thr Ser Ala Asp Val Ala Ser Tyr Arg Leu Lys Gln Gly
        130                 135                 140 ccg att cgt att ctt tcg gcc tgt ggt tct ctg gta gtg gtg gcg ctt       480
Pro Ile Arg Ile Leu Ser Ala Cys Gly Ser Leu Val Val Val Ala Leu
145                 150                 155                 160 tac ctt atc gct cag atg gta ggc gca ggt aaa ctg atc gag ctg ctg       528
Tyr Leu Ile Ala Gln Met Val Gly Ala Gly Lys Leu Ile Glu Leu Leu
                165                 170                 175 ttt ggc ctt aac tat cac att gcg gtg gtg ctg gtc ggc gtg ctg atg       576
Phe Gly Leu Asn Tyr His Ile Ala Val Val Leu Val Gly Val Leu Met
                180                 185                 190 atg atg tac gtc ctg ttc ggc ggc atg ctg gcg acc acc tgg gta caa       624
Met Met Tyr Val Leu Phe Gly Gly Met Leu Ala Thr Thr Trp Val Gln
            195                 200                 205 att atc aaa gct gtg ctg ttg ctg ttc ggt gcc agc ttt atg gcc ttt       672
Ile Ile Lys Ala Val Leu Leu Leu Phe Gly Ala Ser Phe Met Ala Phe
        210                 215                 220 atg gtg atg aaa cac gtc ggc ttt agc ttc aac aat ctg ttc agc gaa       720
Met Val Met Lys His Val Gly Phe Ser Phe Asn Asn Leu Phe Ser Glu
225                 230                 235                 240 gcg atg gcg gta cac ccg aaa ggt gtc gac atc atg aaa ccg ggc gga       768
Ala Met Ala Val His Pro Lys Gly Val Asp Ile Met Lys Pro Gly Gly
                245                 250                 255 ctg gtg aaa gat ccg atc tcc gcg ctc tct ctg ggg ctg gga ctg atg       816
Leu Val Lys Asp Pro Ile Ser Ala Leu Ser Leu Gly Leu Gly Leu Met
                260                 265                 270 ttt ggt acg gcg ggc ttg ccg cac att ctg atg cgc ttc ttt aca gtc       864
Phe Gly Thr Ala Gly Leu Pro His Ile Leu Met Arg Phe Phe Thr Val
            275                 280                 285 agc gat gcc cgc gaa gca cgt aag agc gtg ttc tac gcc acc gga ttt       912
Ser Asp Ala Arg Glu Ala Arg Lys Ser Val Phe Tyr Ala Thr Gly Phe
        290                 295                 300
```

| | | |
|---|---|---|
| atg ggc tac ttc tat att ctg acc ttt att atc ggc ttc ggc gcg atc<br>Met Gly Tyr Phe Tyr Ile Leu Thr Phe Ile Ile Gly Phe Gly Ala Ile<br>305                       310                  315                320 | | 960 |
| atg ctt gtt ggt gcg aat ccg gaa tat aaa gac gcg gcg ggc cat ctg<br>Met Leu Val Gly Ala Asn Pro Glu Tyr Lys Asp Ala Ala Gly His Leu<br>                        325                  330                335 | | 1008 |
| att ggt ggt aac aac atg gcg gcc gtt cac ctg gcg aat gca gtg ggc<br>Ile Gly Gly Asn Asn Met Ala Ala Val His Leu Ala Asn Ala Val Gly<br>                340                345                350 | | 1056 |
| ggc aac cta ttc ctc ggt ttt att tca gcg gtt gct ttc gcc act atc<br>Gly Asn Leu Phe Leu Gly Phe Ile Ser Ala Val Ala Phe Ala Thr Ile<br>                355                360                365 | | 1104 |
| ctc gcg gtg gtt gcg gat ctg acg ctg gcg ggc gca tcg gcg gtt tcg<br>Leu Ala Val Val Ala Asp Leu Thr Leu Ala Gly Ala Ser Ala Val Ser<br>        370                375                380 | | 1152 |
| cat gac ttg tac gct aac gtc ttc aaa aaa ggc gcg acc gaa cgt gaa<br>His Asp Leu Tyr Ala Asn Val Phe Lys Lys Gly Ala Thr Glu Arg Glu<br>385                       390                  395                400 | | 1200 |
| gag ctg cgg gta tca aaa atc acc gta ctg atc ctc ggc gtg att gcg<br>Glu Leu Arg Val Ser Lys Ile Thr Val Leu Ile Leu Gly Val Ile Ala<br>                        405                410                415 | | 1248 |
| att atc ctc ggc gtg ctg ttt gag aat cag aac atc gcc ttt atg gta<br>Ile Ile Leu Gly Val Leu Phe Glu Asn Gln Asn Ile Ala Phe Met Val<br>                420                425                430 | | 1296 |
| ggc ctt gcg ttt gcc atc gcg gcg agc tgt aac ttc ccg atc att ctg<br>Gly Leu Ala Phe Ala Ile Ala Ala Ser Cys Asn Phe Pro Ile Ile Leu<br>              435                440                445 | | 1344 |
| ctt tcc atg tac tgg tcg aaa ctg act acc cgt ggc gcg atg ctg ggc<br>Leu Ser Met Tyr Trp Ser Lys Leu Thr Thr Arg Gly Ala Met Leu Gly<br>        450                455                460 | | 1392 |
| ggc tgg ctg ggg ctg att acc gca gtg gtg ctg atg atc ctc ggc ccg<br>Gly Trp Leu Gly Leu Ile Thr Ala Val Val Leu Met Ile Leu Gly Pro<br>465                       470                  475                480 | | 1440 |
| act att tgg gta cag atc ctc ggt cac gaa aaa gcc atc ttc ccg tat<br>Thr Ile Trp Val Gln Ile Leu Gly His Glu Lys Ala Ile Phe Pro Tyr<br>                        485                490                495 | | 1488 |
| gaa tac ccg gcg ctg ttc tct atc agc gtg gca ttc ctc ggc atc tgg<br>Glu Tyr Pro Ala Leu Phe Ser Ile Ser Val Ala Phe Leu Gly Ile Trp<br>              500                505                510 | | 1536 |
| ttc ttc tcg gca acc gat aac tca gcg gaa ggg gcg cgc gag cgt gaa<br>Phe Phe Ser Ala Thr Asp Asn Ser Ala Glu Gly Ala Arg Glu Arg Glu<br>              515                520                525 | | 1584 |
| ctg ttc cgc gcg cag ttt atc cgc tcc cag acc ggc ttt ggc gtt gag<br>Leu Phe Arg Ala Gln Phe Ile Arg Ser Gln Thr Gly Phe Gly Val Glu<br>        530                535                540 | | 1632 |
| caa ggc cgc gca cat taa<br>Gln Gly Arg Ala His<br>545 | | 1650 |

<210> SEQ ID NO 6
<211> LENGTH: 549
<212> TYPE: PRT
<213> ORGANISM: Shigella flexneri

<400> SEQUENCE: 6

Met Lys Arg Val Leu Thr Ala Leu Ala Ala Thr Leu Pro Phe Ala Ala
1                 5                   10                 15

Asn Ala Ala Asp Ala Ile Ser Gly Ala Val Glu Arg Gln Pro Thr Asn
               20                  25                30

```
Trp Gln Ala Ile Ile Met Phe Leu Ile Phe Val Val Phe Thr Leu Gly
                35                  40                  45

Ile Thr Tyr Trp Ala Ser Lys Arg Val Arg Ser Arg Ser Asp Tyr Tyr
 50                  55                  60

Thr Ala Gly Gly Asn Ile Thr Gly Phe Gln Asn Gly Leu Ala Ile Ala
 65                  70                  75                  80

Gly Asp Tyr Met Ser Ala Ala Ser Phe Leu Gly Ile Ser Ala Leu Val
                 85                  90                  95

Phe Thr Ser Gly Tyr Asp Gly Leu Ile Tyr Ser Leu Gly Phe Leu Val
                100                 105                 110

Gly Trp Pro Ile Ile Leu Phe Leu Ile Ala Glu Arg Leu Arg Asn Leu
                115                 120                 125

Gly Arg Tyr Thr Ser Ala Asp Val Ala Ser Tyr Arg Leu Lys Gln Gly
                130                 135                 140

Pro Ile Arg Ile Leu Ser Ala Cys Gly Ser Leu Val Val Ala Leu
145                 150                 155                 160

Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
                180                 185                 190

Met Met Tyr Val Leu Phe Gly Gly Met Leu Ala Thr Thr Trp Val Gln
                195                 200                 205

Ile Ile Lys Ala Val Leu Leu Leu Phe Gly Ala Ser Phe Met Ala Phe
                210                 215                 220

Met Val Met Lys His Val Gly Phe Ser Phe Asn Asn Leu Phe Ser Glu
225                 230                 235                 240

Ala Met Ala Val His Pro Lys Gly Val Asp Ile Met Lys Pro Gly Gly
                245                 250                 255

Leu Val Lys Asp Pro Ile Ser Ala Leu Ser Leu Gly Leu Gly Leu Met
                260                 265                 270

Phe Gly Thr Ala Gly Leu Pro His Ile Leu Met Arg Phe Phe Thr Val
                275                 280                 285

Ser Asp Ala Arg Glu Ala Arg Lys Ser Val Phe Tyr Ala Thr Gly Phe
                290                 295                 300

Met Gly Tyr Phe Tyr Ile Leu Thr Phe Ile Ile Gly Phe Gly Ala Ile
305                 310                 315                 320

Met Leu Val Gly Ala Asn Pro Glu Tyr Lys Asp Ala Ala Gly His Leu
                325                 330                 335

Ile Gly Gly Asn Asn Met Ala Ala Val His Leu Ala Asn Ala Val Gly
                340                 345                 350

Gly Asn Leu Phe Leu Gly Phe Ile Ser Ala Val Ala Phe Ala Thr Ile
                355                 360                 365

Leu Ala Val Val Ala Asp Leu Thr Leu Ala Gly Ala Ser Ala Val Ser
                370                 375                 380

His Asp Leu Tyr Ala Asn Val Phe Lys Lys Gly Ala Thr Glu Arg Glu
385                 390                 395                 400

Glu Leu Arg Val Ser Lys Ile Thr Val Leu Ile Leu Gly Val Ile Ala
                405                 410                 415

Ile Ile Leu Gly Val Leu Phe Glu Asn Gln Asn Ile Ala Phe Met Val
                420                 425                 430

Gly Leu Ala Phe Ala Ile Ala Ala Ser Cys Asn Phe Pro Ile Ile Leu
                435                 440                 445
```

```
Leu Ser Met Tyr Trp Ser Lys Leu Thr Thr Arg Gly Ala Met Leu Gly
        450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Ser Val Ala Phe Leu Gly Ile Trp
                500                 505                 510

Phe Phe Ser Ala Thr Asp Asn Ser Ala Glu Gly Ala Arg Glu Arg Glu
            515                 520                 525

Leu Phe Arg Ala Gln Phe Ile Arg Ser Gln Thr Gly Phe Gly Val Glu
        530                 535                 540

Gln Gly Arg Ala His
545

<210> SEQ ID NO 7
<211> LENGTH: 26
<212> TYPE: DNA
<213> ORGANISM: Artificial Sequence
<220> FEATURE:
<223> OTHER INFORMATION: Primer yjcG-1
<220> FEATURE:
<221> NAME/KEY: misc_feature
<223> OTHER INFORMATION: Primer yjcG-1

<400> SEQUENCE: 7
gatcaagctt atccggccta cattcg                                          26

<210> SEQ ID NO 8
<211> LENGTH: 31
<212> TYPE: DNA
<213> ORGANISM: Artificial Sequence
<220> FEATURE:
<223> OTHER INFORMATION: Primer yjcG-2
<220> FEATURE:
<221> NAME/KEY: misc_feature
<223> OTHER INFORMATION: Primer yjcg-2

<400> SEQUENCE: 8
gatctagagc tcgattaatg cgcgcggcct t                                    31

<210> SEQ ID NO 9
<211> LENGTH: 2084
<212> TYPE: DNA
<213> ORGANISM: Corynebacterium glutamicum
<220> FEATURE:
<221> NAME/KEY: CDS
<222> LOCATION: (421)..(2067)

<400> SEQUENCE: 9
gatcaagctt atccggccta cattcggcaa gggttacccg agcgttaacc ttctcccata    60
agggagcggg aattaaaaca atccctacat tacctctgga gaatctgtga tgaatggcac   120
tatttatcag cggatagaag acaatgcgca tttcagggag ttagtcgaaa aacggcaacg   180
gtttgccacc atcctgtcga ttattatgct ggcagtttat atcggcttta ttttactgat   240
cgccttcgcg cccggctggc tgggcacgcc gctgaatccg aacaccagcg tcacacgcgg   300
tattccaatt ggtgttggag tgattgtgat ctcctttgtt ctcaccggta tctacatctg   360
gcgggcgaac ggcgaattcg accgtcttaa taatgaagtc ctgcatgagg tacaagcatc   420 atg aaa aga gtt ctg acg gcg ctt gcc gcc aca ctc cct ttc gca gct   468
Met Lys Arg Val Leu Thr Ala Leu Ala Ala Thr Leu Pro Phe Ala Ala
1               5                   10                  15
```

```
aac gcc gcg gat gct att agc ggg gcc gta gag cgc cag cca acg aac      516
Asn Ala Ala Asp Ala Ile Ser Gly Ala Val Glu Arg Gln Pro Thr Asn
            20                  25                  30 tgg cag gcg att att atg ttc ctg att ttc gtc gtg ttt acg ctc ggc      564
Trp Gln Ala Ile Ile Met Phe Leu Ile Phe Val Val Phe Thr Leu Gly
        35                  40                  45 att acc tac tgg gca tca aaa cgc gta cgt tct cgt agc gac tac tac      612
Ile Thr Tyr Trp Ala Ser Lys Arg Val Arg Ser Arg Ser Asp Tyr Tyr
    50                  55                  60 acc gca ggc ggc aat atc act ggc ttc cag aac ggg ctg gcg att gcc      660
Thr Ala Gly Gly Asn Ile Thr Gly Phe Gln Asn Gly Leu Ala Ile Ala
65                  70                  75                  80 ggg gac tat atg tcc gcc gcc tca ttc ttg ggg atc tcc gcg ctg gtg      708
Gly Asp Tyr Met Ser Ala Ala Ser Phe Leu Gly Ile Ser Ala Leu Val
                85                  90                  95 ttt acc tcc ggc tat gac ggc tta att tac tcg ctg ggc ttc ctg gtg      756
Phe Thr Ser Gly Tyr Asp Gly Leu Ile Tyr Ser Leu Gly Phe Leu Val
            100                 105                 110 ggc tgg ccg atc att ttg ttc ctg att gcc gaa cgt ctg cgt aac ctg      804
Gly Trp Pro Ile Ile Leu Phe Leu Ile Ala Glu Arg Leu Arg Asn Leu
        115                 120                 125 ggg cgc tac acc ttt gcc gat gtg gcc tct tac cgt ctg aaa caa ggg      852
Gly Arg Tyr Thr Phe Ala Asp Val Ala Ser Tyr Arg Leu Lys Gln Gly
    130                 135                 140 ccg att cgt att ctt tcg gcc tgt ggt tct ctg gtg gtg gtg gcg ctt      900
Pro Ile Arg Ile Leu Ser Ala Cys Gly Ser Leu Val Val Val Ala Leu
145                 150                 155                 160 tac ctt atc gcc cag atg gtg ggc gca ggt aaa ctg atc gag ctg ctg      948
Tyr Leu Ile Ala Gln Met Val Gly Ala Gly Lys Leu Ile Glu Leu Leu
                165                 170                 175 ttt ggc ctt aac tat cac att gcg gtg gtg ctg gtc ggc gtg ctg atg      996
Phe Gly Leu Asn Tyr His Ile Ala Val Val Leu Val Gly Val Leu Met
            180                 185                 190 atg atg tac gtc ctg ttc ggc ggc atg ctg gcg acc acc tgg gtg caa     1044
Met Met Tyr Val Leu Phe Gly Gly Met Leu Ala Thr Thr Trp Val Gln
        195                 200                 205 att atc aaa gcc gtg ctg ttg ctg ttc ggt gcc agc ttt atg gcc ttt     1092
Ile Ile Lys Ala Val Leu Leu Leu Phe Gly Ala Ser Phe Met Ala Phe
    210                 215                 220 atg gtg atg aaa cac gtc ggc ttt agc ttc aac aat ctg ttc agt gaa     1140
Met Val Met Lys His Val Gly Phe Ser Phe Asn Asn Leu Phe Ser Glu
225                 230                 235                 240 gcg atg gcg gta cac ccg aaa ggt gtc gac atc atg aag ccg ggc ggg     1188
Ala Met Ala Val His Pro Lys Gly Val Asp Ile Met Lys Pro Gly Gly
                245                 250                 255 ctg gtg aaa gat ccg atc tcc gcg ctc tct ctg ggt ctg gga ctg atg     1236
Leu Val Lys Asp Pro Ile Ser Ala Leu Ser Leu Gly Leu Gly Leu Met
            260                 265                 270 ttt ggt acg gcg ggc ttg ccg cac att ctg atg cgc ttc ttt aca gtc     1284
Phe Gly Thr Ala Gly Leu Pro His Ile Leu Met Arg Phe Phe Thr Val
        275                 280                 285 agc gat gcc cgc gaa gca cgt aag agc gtg ttc tac gcc acc ggg ttt     1332
Ser Asp Ala Arg Glu Ala Arg Lys Ser Val Phe Tyr Ala Thr Gly Phe
    290                 295                 300 atg ggc tac ttc tat att ctg acc ttt att atc ggc ttc ggc gcg atc     1380
Met Gly Tyr Phe Tyr Ile Leu Thr Phe Ile Ile Gly Phe Gly Ala Ile
305                 310                 315                 320 atg ctg gtt ggt gcg aat ccg gaa tat aaa gac gcg gcg ggc cat ctg     1428
Met Leu Val Gly Ala Asn Pro Glu Tyr Lys Asp Ala Ala Gly His Leu
                325                 330                 335
```

| | | | | | | | | | | | | | | | | |
|---|---|---|---|---|---|---|---|---|---|---|---|---|---|---|---|---|
| att | ggt | ggt | aac | aac | atg | gcg | gcc | gtt | cac | ctg | gcg | aat | gca | gtg | ggc | 1476 |
| Ile | Gly | Gly | Asn | Asn | Met | Ala | Ala | Val | His | Leu | Ala | Asn | Ala | Val | Gly | |
| | | | 340 | | | | | 345 | | | | | 350 | | | |
| ggc | aac | ctg | ttc | ctc | ggt | ttt | att | tca | gcg | gtt | gct | ttc | gcc | act | atc | 1524 |
| Gly | Asn | Leu | Phe | Leu | Gly | Phe | Ile | Ser | Ala | Val | Ala | Phe | Ala | Thr | Ile | |
| | | 355 | | | | | 360 | | | | | 365 | | | | |
| ctc | gcg | gtg | gtt | gcg | ggt | ctg | acg | ctg | gcg | ggc | gca | tcc | gcg | gtt | tcg | 1572 |
| Leu | Ala | Val | Val | Ala | Gly | Leu | Thr | Leu | Ala | Gly | Ala | Ser | Ala | Val | Ser | |
| 370 | | | | | 375 | | | | | 380 | | | | | | |
| cat | gac | ttg | tac | gct | aac | gtc | ttc | aaa | aaa | ggc | gcg | acc | gaa | cgt | gaa | 1620 |
| His | Asp | Leu | Tyr | Ala | Asn | Val | Phe | Lys | Lys | Gly | Ala | Thr | Glu | Arg | Glu | |
| 385 | | | | | 390 | | | | | 395 | | | | | 400 | |
| gag | ctg | cgg | gta | tca | aaa | atc | acc | gta | ctg | atc | ctc | ggc | gtg | att | gcg | 1668 |
| Glu | Leu | Arg | Val | Ser | Lys | Ile | Thr | Val | Leu | Ile | Leu | Gly | Val | Ile | Ala | |
| | | | | 405 | | | | | 410 | | | | | 415 | | |
| att | atc | ctc | ggc | gtg | ctg | ttt | gag | aat | cag | aac | atc | gcc | ttt | atg | gtg | 1716 |
| Ile | Ile | Leu | Gly | Val | Leu | Phe | Glu | Asn | Gln | Asn | Ile | Ala | Phe | Met | Val | |
| | | | 420 | | | | | 425 | | | | | 430 | | | |
| ggg | ctg | gcg | ttt | gcc | atc | gcg | gcg | agc | tgt | aac | ttc | ccg | atc | att | ctg | 1764 |
| Gly | Leu | Ala | Phe | Ala | Ile | Ala | Ala | Ser | Cys | Asn | Phe | Pro | Ile | Ile | Leu | |
| | | 435 | | | | | 440 | | | | | 445 | | | | |
| ctt | tct | atg | tac | tgg | tcg | aaa | ctg | acc | acg | cgt | ggc | gcg | atg | atg | ggt | 1812 |
| Leu | Ser | Met | Tyr | Trp | Ser | Lys | Leu | Thr | Thr | Arg | Gly | Ala | Met | Met | Gly | |
| | 450 | | | | | 455 | | | | | 460 | | | | | |
| ggc | tgg | ctg | ggg | ctg | att | acc | gca | gta | gta | ctg | atg | atc | ctc | ggc | ccg | 1860 |
| Gly | Trp | Leu | Gly | Leu | Ile | Thr | Ala | Val | Val | Leu | Met | Ile | Leu | Gly | Pro | |
| 465 | | | | | 470 | | | | | 475 | | | | | 480 | |
| acg | att | tgg | gta | cag | atc | ctt | ggt | cac | gaa | aaa | gcc | atc | ttc | ccg | tat | 1908 |
| Thr | Ile | Trp | Val | Gln | Ile | Leu | Gly | His | Glu | Lys | Ala | Ile | Phe | Pro | Tyr | |
| | | | | 485 | | | | | 490 | | | | | 495 | | |
| gaa | tac | ccg | gcg | ctg | ttc | tct | atc | acc | gtg | gca | ttc | ctc | ggc | atc | tgg | 1956 |
| Glu | Tyr | Pro | Ala | Leu | Phe | Ser | Ile | Thr | Val | Ala | Phe | Leu | Gly | Ile | Trp | |
| | | | 500 | | | | | 505 | | | | | 510 | | | |
| ttc | ttc | tcg | gca | acc | gat | aac | tca | gcg | gaa | ggc | gcg | cgt | gag | cgt | gaa | 2004 |
| Phe | Phe | Ser | Ala | Thr | Asp | Asn | Ser | Ala | Glu | Gly | Ala | Arg | Glu | Arg | Glu | |
| | | 515 | | | | | 520 | | | | | 525 | | | | |
| ctg | ttc | cgc | gcg | cag | ttt | atc | cgc | tcc | cag | acc | ggc | ttt | ggc | gtt | gag | 2052 |
| Leu | Phe | Arg | Ala | Gln | Phe | Ile | Arg | Ser | Gln | Thr | Gly | Phe | Gly | Val | Glu | |
| 530 | | | | | 535 | | | | | 540 | | | | | | |
| caa | ggc | cgc | gcg | cat | taatcgagct | ctagatc | | | | | | | | | | 2084 |
| Gln | Gly | Arg | Ala | His | | | | | | | | | | | | |
| 545 | | | | | | | | | | | | | | | | |

<210> SEQ ID NO 10
<211> LENGTH: 549
<212> TYPE: PRT
<213> ORGANISM: Corynebacterium glutamicum

<400> SEQUENCE: 10

Met Lys Arg Val Leu Thr Ala Leu Ala Ala Thr Leu Pro Phe Ala Ala
1               5                   10                  15

Asn Ala Ala Asp Ala Ile Ser Gly Ala Val Glu Arg Gln Pro Thr Asn
                20                  25                  30

Trp Gln Ala Ile Ile Met Phe Leu Ile Phe Val Val Phe Thr Leu Gly
            35                  40                  45

Ile Thr Tyr Trp Ala Ser Lys Arg Val Arg Ser Arg Ser Asp Tyr Tyr
        50                  55                  60

Thr Ala Gly Gly Asn Ile Thr Gly Phe Gln Asn Gly Leu Ala Ile Ala
65                  70                  75                  80

```
Gly Asp Tyr Met Ser Ala Ala Ser Phe Leu Gly Ile Ser Ala Leu Val
                 85                  90                  95

Phe Thr Ser Gly Tyr Asp Gly Leu Ile Tyr Ser Leu Gly Phe Leu Val
            100                 105                 110

Gly Trp Pro Ile Ile Leu Phe Leu Ile Ala Glu Arg Leu Arg Asn Leu
        115                 120                 125

Gly Arg Tyr Thr Phe Ala Asp Val Ala Ser Tyr Arg Leu Lys Gln Gly
    130                 135                 140

Pro Ile Arg Ile Leu Ser Ala Cys Gly Ser Leu Val Val Val Ala Leu
145                 150                 155                 160

Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
            180                 185                 190

Met Met Tyr Val Leu Phe Gly Gly Met Leu Ala Thr Thr Trp Val Gln
        195                 200                 205

Ile Ile Lys Ala Val Leu Leu Leu Phe Gly Ala Ser Phe Met Ala Phe
    210                 215                 220

Met Val Met Lys His Val Gly Phe Ser Phe Asn Asn Leu Phe Ser Glu
225                 230                 235                 240

Ala Met Ala Val His Pro Lys Gly Val Asp Ile Met Lys Pro Gly Gly
                245                 250                 255

Leu Val Lys Asp Pro Ile Ser Ala Leu Ser Leu Gly Leu Gly Leu Met
            260                 265                 270

Phe Gly Thr Ala Gly Leu Pro His Ile Leu Met Arg Phe Phe Thr Val
        275                 280                 285

Ser Asp Ala Arg Glu Ala Arg Lys Ser Val Phe Tyr Ala Thr Gly Phe
    290                 295                 300

Met Gly Tyr Phe Tyr Ile Leu Thr Phe Ile Ile Gly Phe Gly Ala Ile
305                 310                 315                 320

Met Leu Val Gly Ala Asn Pro Glu Tyr Lys Asp Ala Ala Gly His Leu
                325                 330                 335

Ile Gly Gly Asn Asn Met Ala Ala Val His Leu Ala Asn Ala Val Gly
            340                 345                 350

Gly Asn Leu Phe Leu Gly Phe Ile Ser Ala Val Ala Phe Ala Thr Ile
        355                 360                 365

Leu Ala Val Val Ala Gly Leu Thr Leu Ala Gly Ala Ser Ala Val Ser
    370                 375                 380

His Asp Leu Tyr Ala Asn Val Phe Lys Lys Gly Ala Thr Glu Arg Glu
385                 390                 395                 400

Glu Leu Arg Val Ser Lys Ile Thr Val Leu Ile Leu Gly Val Ile Ala
                405                 410                 415

Ile Ile Leu Gly Val Leu Phe Glu Asn Gln Asn Ile Ala Phe Met Val
            420                 425                 430

Gly Leu Ala Phe Ala Ile Ala Ala Ser Cys Asn Phe Pro Ile Ile Leu
        435                 440                 445

Leu Ser Met Tyr Trp Ser Lys Leu Thr Thr Arg Gly Ala Met Met Gly
    450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495
```

```
Glu Tyr Pro Ala Leu Phe Ser Ile Thr Val Ala Phe Leu Gly Ile Trp
            500                 505                 510

Phe Phe Ser Ala Thr Asp Asn Ser Ala Glu Gly Ala Arg Glu Arg Glu
        515                 520                 525

Leu Phe Arg Ala Gln Phe Ile Arg Ser Gln Thr Gly Phe Gly Val Glu
        530                 535                 540

Gln Gly Arg Ala His
545
```